(12) United States Patent
Sasada et al.

(10) Patent No.: US 11,420,930 B2
(45) Date of Patent: Aug. 23, 2022

(54) COMPOSITION FOR LIGHT EMITTING DEVICE AND LIGHT EMITTING DEVICE CONTAINING THE SAME

(71) Applicant: Sumitomo Chemical Company, Limited, Tokyo (JP)

(72) Inventors: Toshiaki Sasada, Tsukuba (JP); Ryuji Matsumoto, Tsukuba (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/969,767

(22) PCT Filed: Dec. 6, 2019

(86) PCT No.: PCT/JP2019/047802
§ 371 (c)(1),
(2) Date: Aug. 13, 2020

(87) PCT Pub. No.: WO2020/137444
PCT Pub. Date: Jul. 2, 2020

(65) Prior Publication Data
US 2021/0309603 A1  Oct. 7, 2021

(30) Foreign Application Priority Data
Dec. 28, 2018  (JP) .............................. JP2018-247484

(51) Int. Cl.
C07C 209/84 (2006.01)
C07C 15/28 (2006.01)
H01L 51/00 (2006.01)
H01L 51/50 (2006.01)
H01L 51/52 (2006.01)

(52) U.S. Cl.
CPC ............ *C07C 209/84* (2013.01); *C07C 15/28* (2013.01); *H01L 51/006* (2013.01); *H01L 51/0054* (2013.01); *H01L 51/0056* (2013.01); *H01L 51/0061* (2013.01); *H01L 51/0072* (2013.01); *H01L 51/5056* (2013.01); *H01L 51/5203* (2013.01)

(58) Field of Classification Search
CPC ............ H01L 51/0052; H01L 51/0054; H01L 51/0055; H01L 51/0056; H01L 51/0057; H01L 51/0058; H01L 51/0059; H01L 51/006; H01L 51/0061; H01L 51/0067; H01L 51/0072; C07C 209/84; C07C 15/27; C07C 15/28; C07C 15/30; C07C 15/38
See application file for complete search history.

(56) References Cited

U.S. PATENT DOCUMENTS

| | | |
|---|---|---|
| 2005/0012450 A1 | 1/2005 | Shinohara et al. |
| 2008/0113468 A1* | 5/2008 | Spreitzer ............. H01L 51/0025 438/99 |
| 2008/0138655 A1 | 6/2008 | Lecloux et al. |
| 2010/0117028 A1 | 5/2010 | Takeshima et al. |
| 2011/0156016 A1 | 6/2011 | Kawamura et al. |
| 2011/0220886 A1 | 9/2011 | Takeshima et al. |
| 2019/0036046 A1 | 1/2019 | Sasada et al. |
| 2020/0203615 A1* | 6/2020 | Sasada ................... C09K 11/06 |

FOREIGN PATENT DOCUMENTS

| | | |
|---|---|---|
| JP | 200541982 A | 2/2005 |
| JP | 2008516421 A | 5/2008 |
| WO | 2010013676 A1 | 2/2010 |
| WO | 2017130977 A1 | 8/2017 |
| WO | 2017170313 A1 | 10/2017 |
| WO | 2018061421 A1 | 4/2018 |

OTHER PUBLICATIONS

Office Action dated Mar. 12, 2019 in JP Application No. 2018247484.
Decision to Grant dated Jul. 31, 2019 in JP Application No. 2018247484.
Extended European Search Report dated Nov. 2, 2020 in EP Application No. 19874762.8.
International Search Report dated Feb. 10, 2020 in International Application No. PCT/JP2019/047802.
Office Action dated Nov. 17, 2020 in CN Application No. 201980005803.7.
Office Action dated Mar. 25, 2021 in CN Application No. 201980005803.7.
Office Action dated Jan. 25, 2022 in JP Application No. 2019162227.

* cited by examiner

*Primary Examiner* — Vu A Nguyen
(74) *Attorney, Agent, or Firm* — Panitch Schwarze Belisario & Nadel LLP

(57) ABSTRACT

A composition useful for the production of a light emitting device showing suppressed initial degradation, and a light emitting device formed by using the composition are provided. The composition contains a blended host material and a guest material, in which the host material contains an aromatic compound having a condensed ring skeleton in which only three or more benzene rings are condensed, the guest material contains an aromatic amine compound, and the total amount of a silicon atom contained in the host material and a silicon atom contained in the guest material is 20 ppm by mass or less with respect to the total amount of the host material and the guest material.

4 Claims, No Drawings

COMPOSITION FOR LIGHT EMITTING DEVICE AND LIGHT EMITTING DEVICE CONTAINING THE SAME

CROSS-REFERENCE TO RELATED APPLICATIONS

This application is a Section 371 of International Application No. PCT/JP2019/047802, filed Dec. 6, 2019, which was published in the Japanese language on Jul. 2, 2020 under International Publication No. WO 2020/137444 A1, which claims priority under 35 U.S.C. § 119(b) to Japanese Application No. 2018-247484, filed on Dec. 28, 2018, the disclosures of which are incorporated herein by reference in their entireties.

TECHNICAL FIELD

The present invention relates to a composition for light emitting device and a light emitting device containing the same.

BACKGROUND ART

Light emitting devices such as an organic electroluminescent device and the like can be suitably used for, for example, displays and illumination. As the material used for a light emitting device, for example, Patent Document 1 proposes a composition containing a compound H0 and a compound EM1.

[Chemical Formula 1]

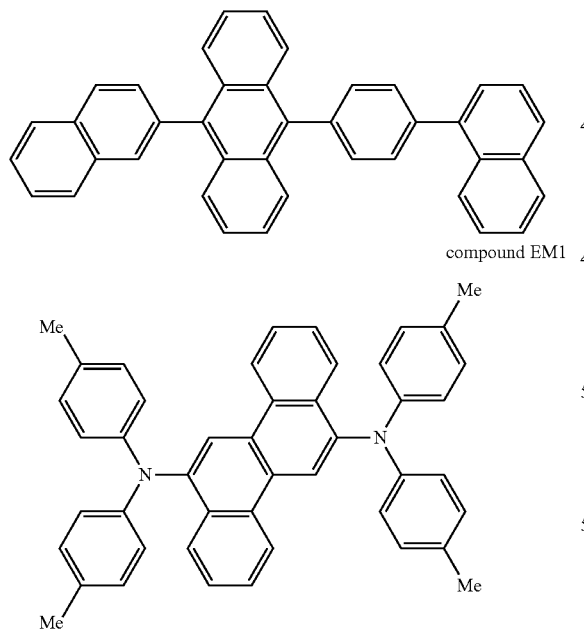

compound H0 compound EM1

PRIOR ART DOCUMENT

Patent Document

[Patent Document 1] International Publication WO 2017/170313

SUMMARY OF THE INVENTION

Problem to be Solved by the Invention

However, in a light emitting device fabricated using the above-described composition, suppression of initial deterioration was not necessarily sufficient.

Then, the present invention has an object of providing a composition useful for producing a light emitting device in which initial deterioration is suppressed, and a light emitting device formed using the composition.

Means for Solving the Problem

The present inventors have intensively studied for solving the above-described problem, and resultantly found that in a light emitting device having an organic layer containing a specific composition, a silicon atom greatly affects the initial deterioration of the light emitting device, and further found that the initial deterioration of the light emitting device can be suppressed by setting the amount of a silicon atom in a specific range, leading to completion of the present invention. In addition, Patent Document 1 does not disclose that the amount of a silicon atom contained in the composition affects the initial deterioration of a light emitting device.

That is, the present invention provides the following [1] to [15].

[1] A composition for light emitting device containing a host material and a guest material blended, wherein
the above-described host material contains an aromatic compound having a condensed ring skeleton in which only three or more benzene rings are condensed,
the above-described guest material contains an aromatic amine compound, and
the total amount of a silicon atom contained in the above-described host material and a silicon atom contained in the above-described guest material is 20 ppm by mass or less with respect to the total amount of the above-described host material and the above-described guest material.

[2] The composition for light emitting device according to [1], wherein the above-described aromatic compound is a compound represented by the formula (FH):

[Chemical Formula 2]

(FH)

[wherein,
$n^{1H}$ represents an integer of 0 or more.
$Ar^{1H}$ represents a group obtained by removing from an aromatic hydrocarbon having a condensed ring skeleton in which only three or more benzene rings are condensed $n^{1H}$ or more hydrogen atoms bonding directly to carbon atoms constituting the condensed ring skeleton, and this group optionally has a substituent. When a plurality of the substituents are present, they may be the same or different and may be combined together to form a ring together with atoms to which they are attached.
$R^{1H}$ represents an aryl group or a monovalent heterocyclic group, and the foregoing groups optionally have a substituent. When a plurality of the substituents are present, they may be the same or different and may be combined together to form a ring together with atoms to which they are attached. When a plurality of RIF' are present, they may be the same or different and may be combined together to form a ring together with atoms to which they are attached.].

[3] The composition for light emitting device according to [1] or [2], wherein the above-described condensed ring skeleton is a condensed ring skeleton in which only 3 or more and 5 or less benzene rings are condensed.

[4] The composition for light emitting device according to [3], wherein the above-described condensed ring skeleton is an anthracene skeleton, a phenanthrene skeleton, a benzoanthracene skeleton, a benzophenanthrene skeleton or a pyrene skeleton.

[5] The composition for light emitting device according to any one of [1] to [4], wherein the above-described aromatic amine compound is a compound represented by the formula (FB):

[Chemical Formula 3]

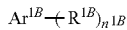  (FB)

[wherein, $n^{1B}$ represents an integer of 1 or more.

$Ar^{1B}$ represents an aromatic hydrocarbon group or an aromatic heterocyclic group, and the foregoing groups optionally have a substituent. When a plurality of the substituents are present, they may be the same or different and may be combined together to form a ring together with atoms to which they are attached.

$R^{1B}$ represents an amino group or a substituted amino group, and the foregoing groups optionally have a substituent. When a plurality of the substituents are present, they may be the same or different and may be combined together to form a ring together with atoms to which they are attached. When a plurality of $R^{1B}$ are present, they may be the same or different and may be combined together to form a ring together with atoms to which they are attached.].

[6] The composition for light emitting device according to any one of [1] to [5], further comprising at least one selected from group consisting of a hole transporting material, a hole injection material, an electron transporting material, an electron injection material, a light emitting material, an antioxidant and a solvent.

[7] A light emitting device having an anode, a cathode, and an organic layer disposed between the above-described anode and the above-described cathode, wherein the above-described organic layer is a layer containing the composition for light emitting device according to any one of [1] to [6].

[8] A method of producing a composition for light emitting device containing a host material and a guest material blended, including a host material preparation step of preparing a host material containing an aromatic compound having a condensed ring skeleton in which only three or more benzene rings are condensed, a guest material preparation step of preparing a guest material containing an aromatic amine compound, and a production step of mixing the above-described host material and the above-described guest material at a compounding ratio by which the total amount of a silicon atom contained in the above-described host material and a silicon atom contained in the above-described guest material is 20 ppm by mass or less, to obtain a composition for light emitting device.

[9] The production method according to [8], wherein the above-described guest material preparation step includes a preparation step (B-1) of preparing the above-described aromatic amine compound containing a silicon atom mixed therein, and a step (B-2) of purifying at least a part of the above-described aromatic amine compound prepared in the above-described step (B-1) to remove at least a part of the above-described silicon atom.

[10] The production method according to [8] or [9], wherein the above-described host material preparation step includes a step (A-1) of preparing the above-described aromatic compound containing a silicon atom mixed therein, and a step (A-2) of purifying at least a part of the above-described aromatic compound prepared in the above-described step (A-1) to remove at least a part of the above-described silicon compound.

[11] A method of producing a composition for light emitting device containing a host material and a guest material blended, including a host material preparation step of preparing a host material containing an aromatic compound having a condensed ring skeleton in which only three or more benzene rings are condensed, a determination step of determining the compounding ratio of the above-described guest material with respect to the above-described host material, a guest material preparation step of preparing a guest material containing an aromatic amine compound and in which, when mixed with the above-described host material at the above-described compounding ratio, the total amount of a silicon atom contained in the above-described host material and a silicon atom contained in the above-described guest material with respect to the total amount of the above-described host material and the above-described guest material is 20 ppm by mass or less, and a production step of mixing the above-described host material and the above-described guest material at the above-described compounding ratio, to obtain a composition for light emitting device.

[12] A method of producing a composition for light emitting device containing a host material and a guest material blended, including a guest material preparation step of preparing a guest material containing an aromatic amine compound, a determination step of determining the compounding ratio of the above-described host material with respect to the above-described guest material, a host material preparation step of preparing a host material containing an aromatic compound having a condensed ring skeleton in which only three or more benzene rings are condensed and in which, when mixed with the above-described guest material at the above-described compounding ratio, the total amount of a silicon atom contained in the above-described host material and a silicon atom contained in the above-described guest material with respect to the total amount of the above-described host material and the above-described guest material is 20 ppm by mass or less, and a production step of mixing the above-described guest material and the above-described host material at the above-described compounding ratio, to obtain a composition for light emitting device.

[13] A method of producing a composition for light emitting device containing a host material and a guest material blended, including a host material preparation step of preparing an aromatic compound having a condensed ring skeleton in which only three or more benzene rings are condensed as the host material, a guest material preparation step of preparing an aromatic amine compound as the guest material, a determination step of determining the compounding ratio of the above-described host material and the above-described guest material, a purification step of purifying at least a part of the above-described aromatic compound and the above-described aromatic amine compound so that, when the above-described host material and the above-described guest material are mixed at the above-described compounding ratio, the total amount of a silicon atom contained in the above-described host material and a silicon atom contained in the above-described guest material with respect to the total amount of the above-described host material and the above-described guest material is 20 ppm by mass or less, and a production step of mixing the above-described host material containing the above-described aromatic compound and the above-described guest material containing the above-described aromatic amine compound at the above-described compounding ratio, to obtain a composition for light emitting device.

[14] The production method according to any one of [8] to [13], further including a host material measurement step of measuring the content of a silicon atom contained in the above-described aromatic compound, and a gust material measurement step of measuring the content of a silicon atom contained in the above-described aromatic amine compound.

[15] A method of producing a light emitting device containing an anode, a cathode and an organic layer disposed between the above-described anode and the above-described cathode, comprising a step of forming the above-described organic layer from a composition for light emitting device produced by the production method according to any one of [8] to [14].

Effect of the Invention

According to this invention, a composition which is useful for production of a light emitting device in which the initial deterioration is suppressed can be provided. Further, according to the present invention, a light emitting device containing the above-described composition can be provided. Further, according to the present invention, a method for producing the above-described composition and the above-described light emitting device can be provided.

MODES FOR CARRYING OUT THE INVENTION

Hereinafter, preferred embodiments of the present embodiment will be described in detail.

Explanation of Common Terms

Terms commonly used in the present specification have the following meanings unless otherwise stated.

"Room temperature" denotes 25° C.

Me represents a methyl group, Et represents an ethyl group, Bu represents a butyl group, i-Pr represents an isopropyl group and t-Bu represents a tert-butyl group.

The hydrogen atom may be a heavy hydrogen atom or a light hydrogen atom.

"Polymer compound" denotes a polymer having molecular weight distribution and having a polystyrene-equivalent number-average molecular weight of $1 \times 10^3$ to $1 \times 10^8$.

"Low molecular compound" denotes a compound having no molecular weight distribution and having a molecular weight of $1 \times 10^4$ or less.

"Constitutional unit" denotes a unit occurring once or more times in the polymer compound.

"Alkyl group" may be any of linear and branched. The number of carbon atoms of the linear alkyl group, not including the number of carbon atoms of the substituent, is usually 1 to 50, preferably 1 to 20, and more preferably 1 to 10. The number of carbon atoms of the branched alkyl group, not including the number of carbon atoms of the substituent, is usually 3 to 50, preferably 3 to 20, and more preferably 4 to 10. The alkyl group optionally has a substituent and examples thereof include, for example, a methyl group, an ethyl group, an isopropyl group, a butyl group, an isobutyl group, a tert-butyl group, a pentyl group, a hexyl group, a heptyl group, an octyl group, a 2-ethylhexyl group, a decyl group, a 3,7-dimethyloctyl group, a 2-ethyloctyl group, a dodecyl group, a trifluoromethyl group, a 3-phenylpropyl group, a 3-(4-methylphenyl)propyl group, a 3-(3,5-di-hexylphenyl)propyl group and a 6-ethyloxyhexyl group.

The number of carbon atoms of "cycloalkyl group", not including the number of carbon atoms of the substituent, is usually 3 to 50, and preferably 4 to 10. The cycloalkyl group optionally has a substituent and examples thereof include a cyclohexyl group and a methylcyclohexyl group.

The number of carbon atoms of "alkylene group", not including the number of carbon atoms of the substituent, is usually 1 or more and 20 or less, preferably 1 or more and 15 or less, and more preferably 1 or more and 10 or less. The alkylene group optionally has a substituent and examples thereof include a methylene group, an ethylene group, a propylene group, a butylene group, a hexylene group and an octylene group.

The number of carbon atoms of "cycloalkylene group", not including the number of carbon atoms of the substituent, is usually 3 or more and 20 or less. The cycloalkylene group optionally has a substituent and examples thereof include a cyclohexylene group.

"Aromatic hydrocarbon group" denotes a group obtained by removing from an aromatic hydrocarbon one or more hydrogen atoms bonding directly to carbon atoms constituting the ring. A group obtained by removing from an aromatic hydrocarbon one hydrogen atom bonding directly to a carbon atom constituting the ring is referred to also as "aryl group". A group obtained by removing from an aromatic hydrocarbon two hydrogen atoms bonding directly to carbon atoms constituting the ring is referred to also as "arylene group".

The number of carbon atoms of the aromatic hydrocarbon group, not including the number of carbon atoms of the substituent, is usually 6 to 60, preferably 6 to 30, and more preferably 6 to 18.

"Aromatic hydrocarbon group" includes, for example, groups obtained by removing from mono-cyclic aromatic hydrocarbons (including, for example, benzene) or polycyclic aromatic hydrocarbons (including, for example, bicyclic aromatic hydrocarbons such as naphthalene, indene and the like; tri-cyclic aromatic hydrocarbons such as anthracene, phenanthrene, dihydrophenanthrene, fluorene and the like; tetra-cyclic aromatic hydrocarbons such as benzoanthracene, benzophenanthrene, benzofluorene, pyrene, fluoranthene and the like; penta-cyclic aromatic hydrocarbons such as dibenzoanthracene, dibenzophenanthrene, dibenzofluorene, perylene, benzofluoranthene and the like; hexa-cyclic aromatic hydrocarbons such as spirobifluorene and the like; and hepta-cyclic aromatic hydrocarbons such as benzospirobifluorene, acenaphthofluoranthene and the like) one or more hydrogen atoms bonding directly to carbon atoms constituting the ring, and the foregoing groups optionally have a substituent. The aromatic hydrocarbon group includes groups obtained by bonding a plurality of these groups.

"Alkoxy group" may be any of linear and branched. The number of carbon atoms of the linear alkoxy group, not including the number of carbon atoms of the substituent, is usually 1 to 40, and preferably 1 to 10. The number of carbon atoms of the branched alkoxy group, not including the number of carbon atoms of the substituent, is usually 3 to 40, and preferably 4 to 10. The alkoxy group optionally has a substituent and includes, for example, a methoxy group, an ethoxy group, an isopropyloxy group, a butyloxy group, a hexyloxy group, a 2-ethylhexyloxy group, 3,7-dimethyloctyloxy group and a lauryloxy group.

The number of carbon atoms of "cycloalkoxy group", not including the number of carbon atoms of the substituent, is usually 3 to 40, and preferably 4 to 10. The cycloalkoxy group optionally has a substituent and includes, for example, a cyclohexyloxyl group.

The number of carbon atoms of "aryloxy group", not including the number of carbon atoms of the substituent, is usually 6 to 60, and preferably 6 to 48. The aryloxy group optionally has a substituent and includes, for example, a phenoxy group, a naphthyloxy group, an anthracenyloxyl group and a pyrenyloxy group.

"Heterocyclic group" denotes a group obtained by removing from a heterocyclic compound one or more hydrogen atoms bonding directly to carbon atoms or hetero atoms constituting the ring. Of heterocyclic groups, preferable is "aromatic heterocyclic group" which is a group obtained by removing from an aromatic heterocyclic compound one or more hydrogen atoms bonding directly to carbon atoms or hetero atoms constituting the ring. A group obtained by removing from a heterocyclic compound p hydrogen atoms bonding directly to carbon atoms or hetero atoms constituting the ring (p represents an integer of 1 or more.) is also referred to as "p-valent heterocyclic group". A group obtained by removing from an aromatic heterocyclic compound p hydrogen atoms bonding directly to carbon atoms or hetero atoms constituting the ring is also referred to as "p-valent aromatic heterocyclic group".

"Aromatic heterocyclic compound" includes, for example, compounds in which the heterocyclic ring itself shows aromaticity such as azole, thiophene, furan, pyridine, diazabenzene, triazine, azanaphthalene, diazanaphthalene, carbazole and the like, and compounds in which an aromatic ring is condensed to a heterocyclic ring even if the heterocyclic ring itself shows no aromaticity such as phenoxazine, phenothiazine, benzopyran and the like.

The number of carbon atoms of the heterocyclic group, not including the number of carbon atoms of the substituent, is usually 1 to 60, preferably 2 to 40, and more preferably 3 to 20. The number of the hetero atom of the heterocyclic group, not including the number of carbon atoms of the substituent, is usually 1 to 30, preferably 1 to 10, and more preferably 1 to 3.

The heterocyclic group optionally has a substituent and includes, for example, groups obtained by removing from a mono-cyclic heterocyclic compound (including, for example, furan, thiophene, oxadiazole, pyrrole, diazole, triazole, tetrazole, pyridine, diazabenzene and triazine) or a poly-cyclic heterocyclic compound (including, for example, bi-cyclic heterocyclic compounds such as azanaphthalene, diazanaphthalene, benzofuran, benzothiophene, indole, benzodiazole, benzothiadiazole and the like; tri-cyclic heterocyclic compounds such as dibenzofuran, dibenzothiophene, dibenzoborole, dibenzosilole, dibenzophosphole, dibenzoselenophene, carbazole, azacarbazole, diazacarbazole, phenoxazine, phenothiazine, 9,10-dihydroacridine, 5,10-dihydrophenazine, phenazaborine, phenophosphazine, phenoselenazine, phenazacillin, azaanthracene, diazaanthracene, azaphenanthrene, diazaphenanthrene and the like; tetra-cyclic heterocyclic compounds such as hexaazatriphenylene, benzocarbazole, benzonaphthofuran, benzonaphthothiophene and the like; penta-cyclic heterocyclic compounds such as dibenzocarbazole, indolocarbazole, indenocarbazole and the like; hexa-cyclic heterocyclic compounds such as carbazolocarbazole, benzoindrocarbazole, benzoindenocarbazole and the like; and hepta-cyclic heterocyclic compounds such as dibenzoindrocarbazole and the like) one or more hydrogen atoms bonding directly to atoms constituting the ring, and the foregoing groups optionally have a substituent. The heterocyclic group includes groups obtained by bonding a plurality of these groups.

"Halogen atom" denotes a fluorine atom, a chlorine atom, a bromine atom or an iodine atom.

"Amino group" optionally has a substituent, and substituted amino groups (namely, secondary amino groups or tertiary amino groups, preferably, tertiary amino groups) are preferred. As the substituent which an amino group has, an alkyl group, a cycloalkyl group, an aryl group or a monovalent heterocyclic group is preferable. When a plurality of the substituents which an amino group has are present, they may be the same or different and may be combined together to form a ring together with nitrogen atoms to which they are attached.

The substituted amino group includes, for example, a dialkylamino group, a dicycloalkylamino group and a diarylamino group.

The amino group includes, for example, a dimethylamino group, a diethylamino group, a diphenylamino group, a bis(methylphenyl)amino group and a bis(3,5-di-tert-butylphenyl)amino group.

"Alkenyl group" may be any of linear and branched. The number of carbon atoms of the linear alkenyl group, not including the number of carbon atoms of the substituent, is usually 2 to 30, and preferably 3 to 20. The number of carbon atoms of the branched alkenyl group, not including the number of carbon atoms of the substituent, is usually 3 to 30, and preferably 4 to 20.

The number of carbon atoms of the "cycloalkenyl group", not including the number of carbon atoms of the substituent, is usually 3 to 30, and preferably 4 to 20.

The alkenyl group and the cycloalkenyl group optionally have a substituent and examples thereof include a vinyl group, a 1-propenyl group, a 2-propenyl group, a 2-butenyl group, a 3-butenyl group, a 3-pentenyl group, a 4-pentenyl group, a 1-hexenyl group, a 5-hexenyl group and a 7-octenyl group, and these groups having a substituent.

"Alkynyl group" may be any of linear and branched. The number of carbon atoms of the alkynyl group, not including the number of carbon atoms of the substituent, is usually 2 to 20, and preferably 3 to 20. The number of carbon atoms of the branched alkynyl group, not including the number of carbon atoms of the substituent, is usually 4 to 30, and preferably 4 to 20.

The number of carbon atoms of the "cycloalkynyl group", not including the number of carbon atoms of the substituent, is usually 4 to 30, and preferably 4 to 20.

The alkynyl group and the cycloalkynyl group optionally have a substituent and examples thereof include an ethynyl group, a propynyl group, a butynyl group, a pentynyl group, a hexynyl group and a 5-hexynyl group, and these groups having a substituent.

"Crosslinkable group" refers to a group capable of generating a new bond by being subjected to a heating treatment, an ultraviolet irradiation treatment, a near-ultraviolet irradiation treatment, a visible light irradiation treatment, an infrared irradiation treatment, a radical reaction and the like, and is preferably a group represented by any of the formula (B-1) to the formula (B-17). The foregoing groups optionally have a substituent.

[Chemical Formula 4]

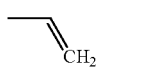
(B-1)

(B-2)

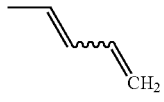
(B-3)

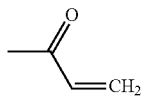
(B-4)

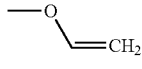
(B-5)

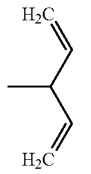
(B-6)

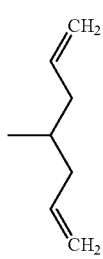
(B-7)

-continued

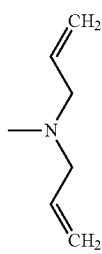
(B-8)

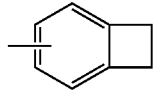
(B-9)

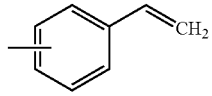
(B-10)

(B-11)

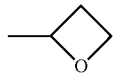
(B-12)

(B-13)

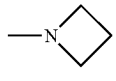
(B-14)

(B-15)

(B-16)

(B-17)

"Substituent" includes, for example, a halogen atom, a cyano group, an alkyl group, a cycloalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group and a cycloalkynyl group. The substituent may be a crosslinkable group. When a plurality of substituents are present, they may be combined together to form a ring together with atoms to which they are attached, however, it is preferable that they do not form a ring.

"Amount of silicon atom" can be measured by an ICP emission spectroscopic analysis method (inductively coupled plasma emission spectrometry). That is, "amount of silicon atom" denotes the mass concentration of a silicon atom as measured by an ICP emission spectroscopic analysis method. Further, when "amount of silicon atom" is "0 ppm by mass", it means that the mass concentration of a silicon atom is below the detection limit when measured by an ICP emission spectroscopic analysis method.

In the composition for light emitting device of the present embodiment, the host material means a material that physically, chemically or electrically interacts with the guest material. By this interaction, for example, it becomes possible to improve or adjust the light emission characteristics, charge transport characteristics or charge injection characteristics of the composition for light emitting device of the present embodiment.

In the composition for light emitting device of the present embodiment, when explained taking a light emitting material as an example, the host material and the guest material electrically interact with each other and electric energy is transferred efficiently from the host material to the guest material, so that the guest material can emit light more efficiently.

<Host Material>

The host material contains an aromatic compound having a condensed ring skeleton in which only three or more benzene rings are condensed. The aromatic compound having a condensed ring skeleton in which only three or more benzene rings are condensed may contain only one type of the condensed ring skeleton in which only three or more benzene rings are condensed, or may contain two or more types of the condensed ring skeletons. Further, the aromatic compound having a condensed ring skeleton in which only three or more benzene rings are condensed may contain only one type of the condensed ring skeleton in which only three or more benzene rings are condensed, or two or more types of the condensed ring skeletons, in the compound. Hereinafter, the aromatic compound having a condensed ring skeleton in which only three or more benzene rings are condensed contained in the host material may be referred to as "aromatic compound for host material" in some cases.

In the condensed ring skeleton of the aromatic compound for host material, the number of condensed benzene rings is usually 3 to 10, and since the initial deterioration of the light emitting device of the present embodiment is more suppressed, it is preferably 3 to 7, more preferably 3 to 5, and even more preferably 3 or 4.

The condensed ring skeleton of the aromatic compound for host material can be said to be a carbon skeleton of a condensed ring in which only three or more benzene rings are condensed. The condensed ring skeleton is preferably an anthracene skeleton, a phenanthrene skeleton, a benzoanthracene skeleton, a benzophenanthrene skeleton or a pyrene skeleton, more preferably an anthracene skeleton, benzoanthracene skeleton or a pyrene skeleton, and further preferably an anthracene skeleton, because the initial deterioration of the light emitting device of the present embodiment is more suppressed.

The aromatic compound for host material may be an aromatic hydrocarbon having a condensed ring skeleton in which only three or more benzene rings are condensed (hereinafter, also referred to as "condensed ring-containing aromatic hydrocarbon"), and the aromatic hydrocarbon optionally has a substituent. The substituent which the condensed ring-containing aromatic hydrocarbon optionally has is preferably a halogen atom, an alkyl group, a cycloalkyl group, an alkoxy group, a cycloalkoxy group, an aryl group, a monovalent heterocyclic group or a substituted amino group, more preferably an alkyl group, cycloalkyl group, an aryl group or a monovalent heterocyclic group, further preferably an aryl group or a monovalent heterocyclic group, particularly preferably an aryl group, and the foregoing groups optionally further have a substituent.

In the substituent which the condensed ring-containing aromatic hydrocarbon optionally has, the aryl group is preferably a group obtained by removing from a monocyclic or bicyclic to hexa-cyclic aromatic hydrocarbon one or more hydrogen atoms bonding directly to carbon atoms constituting the ring, more preferably a group obtained by removing from a monocyclic or bicyclic to tetracyclic aromatic hydrocarbon one or more hydrogen atoms bonding directly to carbon atoms constituting the ring, further preferably a group obtained by removing from benzene, naphthalene, dihydrophenanthrene, fluorene or benzofluorene one or more hydrogen atoms bonding directly to carbon atoms constituting the ring, and particularly preferably a phenyl group or a naphthyl group, and the foregoing groups optionally have a substituent.

In the substituent which the condensed ring-containing aromatic hydrocarbon optionally has, the monovalent heterocyclic group is preferably a group obtained by removing from a monocyclic or bicyclic to hexa-cyclic heterocyclic compound one or more hydrogen atoms bonding directly to atoms constituting the ring, more preferably a group obtained by removing from a monocyclic or bicyclic to tetracyclic heterocyclic compound one or more hydrogen atoms bonding directly to atoms constituting the ring, further preferably a group obtained by removing from pyridine, diazabenzene, triazine, azanaphthalene, diazanaphthalene, dibenzofuran, dibenzothiophene, carbazole, benzocarbazole, banzonaphthofuran or benzonaphthothiophene one or more hydrogen atoms bonding directly to atoms constituting the ring, and the foregoing groups optionally have a substituent.

In the substituted amino group as the substituent which the condensed ring-containing aromatic hydrocarbon optionally has, the substituent of the amino group is preferably an aryl group or a monovalent heterocyclic group, more preferably an aryl group, and the foregoing groups optionally further have a substituent. The examples and preferable ranges of the aryl group which is the substituent of the amino group are the same as the examples and preferable ranges of the aryl group as the substituent which the condensed ring-containing aromatic hydrocarbon optionally has. The examples and preferable ranges of the monovalent heterocyclic group which is the substituent of the amino group are the same as the examples and preferable ranges of the monovalent heterocyclic group as the substituent which the condensed ring-containing aromatic hydrocarbon optionally has.

The condensed ring-containing aromatic hydrocarbon preferably has a substituent since the initial deterioration of the light emitting device of the present embodiment is more suppressed. When the condensed ring-containing aromatic hydrocarbon has a substituent, the total number of the substituents which the condensed ring-containing aromatic hydrocarbon has usually 1 to 20 (providing it is not higher than the total number of hydrogen atoms which the condensed ring-containing aromatic hydrocarbon has, the same shall apply hereinafter), and since synthesis of the host material is easy, the number is preferably 1 to 15, more preferably 1 to 10, further preferably from 1 to 7, particularly preferably from 1 to 5, and especially preferably from 1 to 3.

The substituent which the substituent which the condensed ring-containing aromatic hydrocarbon optionally has optionally further has is preferably a halogen atom, an alkyl group, a cycloalkyl group, an alkoxy group, a cycloalkoxy group, an aryl group, a monovalent heterocyclic group or a substituted amino group, more preferably an alkyl group, a cycloalkyl group, an aryl group, a monovalent heterocyclic group or a substituted amino group, and further preferably an alkyl group or a cycloalkyl group, and the foregoing groups optionally further have a substituent, however, it is preferable that they do not have a substituent.

The examples and preferable ranges of the aryl group, the monovalent heterocyclic group and the substituted amino group as the substituent which the substituent which the condensed ring-containing aromatic hydrocarbon optionally has optionally further has are the same as the examples and the preferable range of the aryl group, the monovalent heterocyclic group and the substituted amino group as the substituent which the ring-containing aromatic hydrocarbon optionally has, respectively.

The host material may further contain a compound other than the aromatic compound for host material, however, since the initial deterioration of the light emitting device of the present embodiment is more suppressed, it is preferable that the aromatic compound for host material is contained as the main component. The content ratio of the aromatic compound for host material in the host material may be, for example, 10% by mass or more, and since the initial deterioration of the light emitting device of the present embodiment is more suppressed, it is preferably 30% by mass or more, more preferably 50% by mass or more, further preferably 70% by mass or more, particularly preferably 90% by mass or more, and especially preferably 95% by mass or more, and may also be 100% by mass.

The host material may contain only one type of the aromatic compound for host material, or may contain two or more types of the aromatic compounds for host material. When the host material further contains a compound other than the aromatic compound for host material, the host material may contain only one type of the compound other than the aromatic compound for host material, or may contain two or more types of the compounds other than the aromatic compound for host material.

The aromatic compound for host material may be a polymer compound (hereinafter, referred to also as "polymer host material") or may be a low molecular compound (hereinafter, referred to also as "low molecular host material"), and the low molecular host material is preferred.

(Low Molecular Host Material)

The molecular weight of the low molecular host material is usually $1\times10^2$ to $1\times10^4$, preferably $2\times10^2$ to $5\times10^3$, more preferably $3\times10^2$ to $2\times10^3$, and further preferably $4\times10^2$ to $1\times10^3$.

The total number of condensed ring skeletons in which only three or more benzene rings are condensed contained in the low molecular host material is usually 1 to 10, and since the initial degradation of the light emitting device of the present embodiment is more suppressed, it is preferably 1 to 7, more preferably 1 to 5, further preferably 1 to 3, and particularly preferably 1.

The low molecular host material may contain only one type of the condensed ring skeleton in which only three or more benzene rings are condensed or may contain 2 or more types of the skeletons, and since synthesis of the low molecular host material is easy, it contains preferably 1 to 5 types of the skeletons, more preferably 1 to 3 types of the skeletons, and further preferably 1 type of the skeleton.

It is preferable that the low molecular host material contains a condensed ring skeleton in which only three or more benzene rings are condensed as a group obtained by removing from an aromatic hydrocarbon having a condensed ring skeleton in which only three or more benzene rings are condensed one or more hydrogen atoms bonding directly to carbon atoms constituting the condensed ring skeleton (hereinafter, referred to also as "condensed ring-containing aromatic hydrocarbon group"), since the initial degradation of the light emitting device of the present embodiment is more suppressed, and this group optionally has a substituent.

The total number of the condensed ring-containing aromatic hydrocarbon group contained in the low molecular host material is usually 1 to 10, and since the initial degradation of the light emitting device of the present embodiment is more suppressed, it is preferably 1 to 7, more preferably 1 to 5, further preferably 1 to 3, and particularly preferably 1.

The low molecular host material may contain only one type of the condensed ring-containing aromatic hydrocarbon group, or may contain two or more types, and since synthesis of the low molecular host material is easy, it may contain preferably 1 to 5 types of the groups, more preferably 1 to 3 types of the groups, and further preferably 1 type of the group.

In the low molecular host material, the examples and preferable ranges of the substituent which the condensed ring-containing aromatic hydrocarbon group optionally has are the same as the examples and preferable ranges of the substituent which the condensed ring-containing aromatic hydrocarbon optionally has.

[Compound Represented by the Formula (FH)]

The low molecular host material is preferably a compound represented by the formula (FH), since the initial degradation of the light emitting device of the present embodiment is more suppressed.

$n^{1H}$ is usually an integer of 10 or less, and since synthesis of the compound represented by the formula (FH) is easy, it is preferably an integer of 7 or less, more preferably an integer of 5 or less, and further preferably an integer of 3 or less. Further, $n^{1H}$ is preferably an integer of 1 or more, since the initial deterioration of the light emitting device of this embodiment is more suppressed.

In $Ar^{1H}$, the substituent that the condensed ring-containing aromatic hydrocarbon group optionally has is a substituent other than an aryl group and a monovalent heterocyclic group, and is preferably a halogen atom, an alkyl group, a cycloalkyl group, an alkoxy group, a cycloalkoxy group or a substituted amino group, more preferably an alkyl group or a cycloalkyl group, and the foregoing groups optionally further have a substituent.

The examples and preferable ranges of the substituted amino group as the substituent which the condensed ring-containing aromatic hydrocarbon group optionally has are the same as the examples and preferable range of the substituted amino group as the substituent which the condensed ring-containing aromatic hydrocarbon optionally has.

The examples and preferable ranges of the substituent which the substituent which the condensed ring-containing aromatic hydrocarbon group optionally has optionally further has are the same as the examples and preferable ranges of the substituent which the substituent which the condensed ring-containing aromatic hydrocarbon optionally has optionally further has.

$R^{1H}$ is preferably an aryl group optionally having a substituent, since the initial deterioration of the light emitting device of this embodiment is more suppressed.

The examples and preferable ranges of the aryl group and the monovalent heterocyclic group for $R^{1H}$ are the same as the examples and preferable range of the aryl group and the monovalent heterocyclic group as the substituent which the condensed ring-containing aromatic hydrocarbon optionally has, respectively.

The examples and preferable ranges of the substituent which $R^{1H}$ optionally has are the same as the examples and preferable ranges of the substituent which the substituent which the condensed ring-containing aromatic hydrocarbon optionally has optionally further has.

Examples of the low molecular host material include compounds represented by the following formulas and compounds described in Examples. These compounds optionally have a substituent. In the formula, $Z^1$ represents an oxygen atom or a sulfur atom. When a plurality of $Z^1$ are present, they may be the same or different.

[Chemical Formula 5]

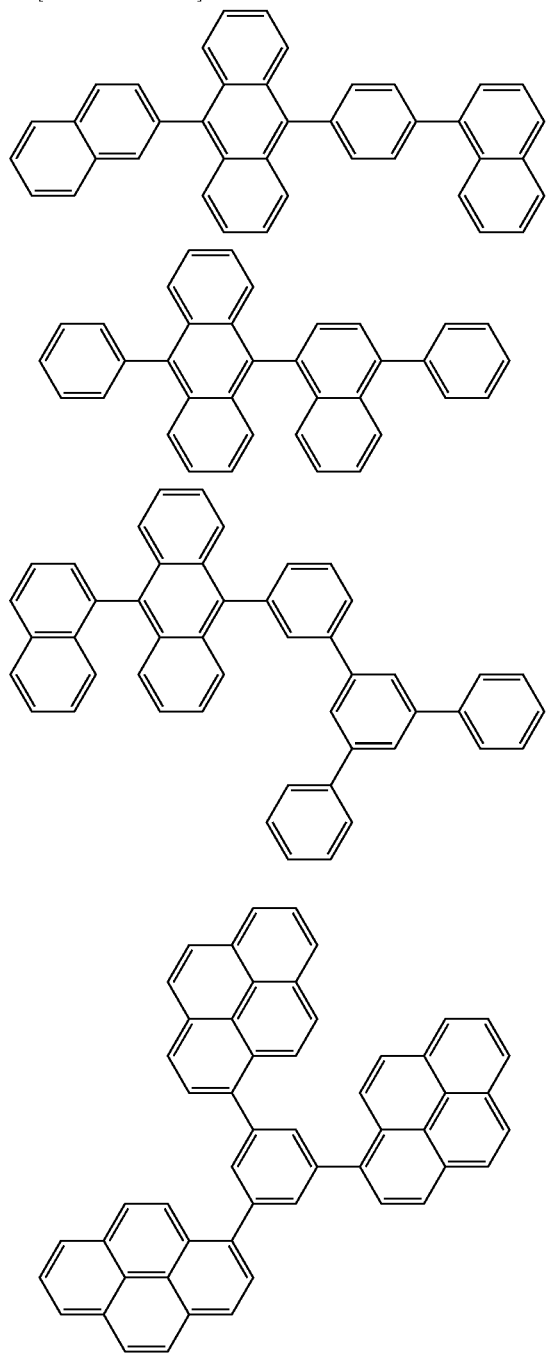

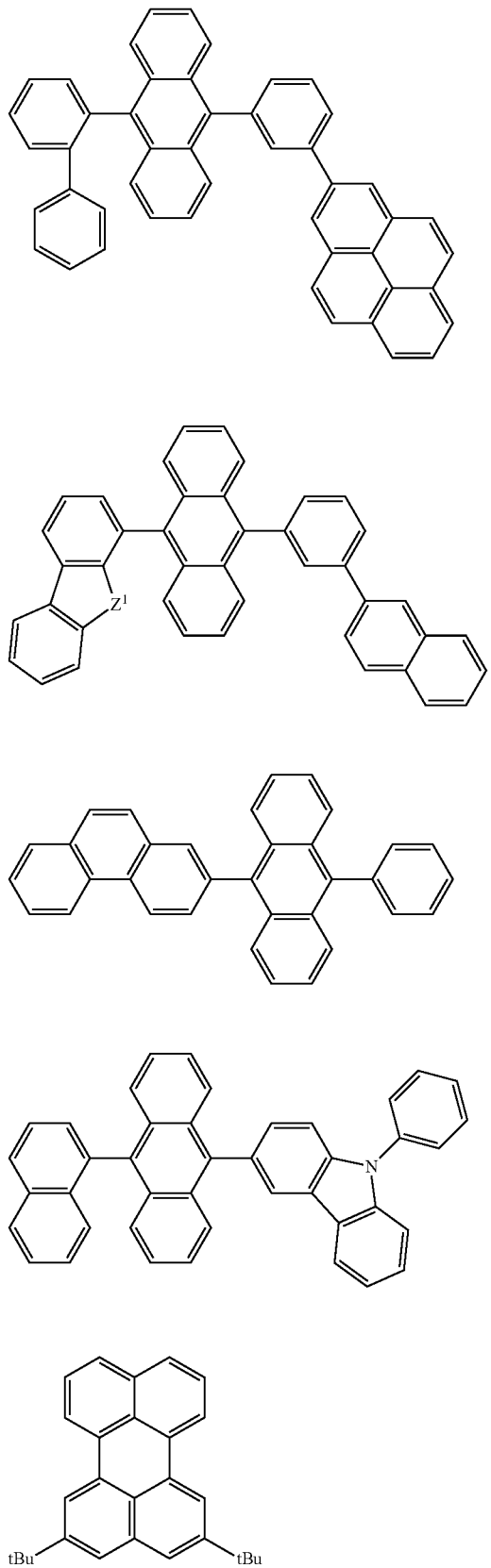

[Chemical Formula 6]

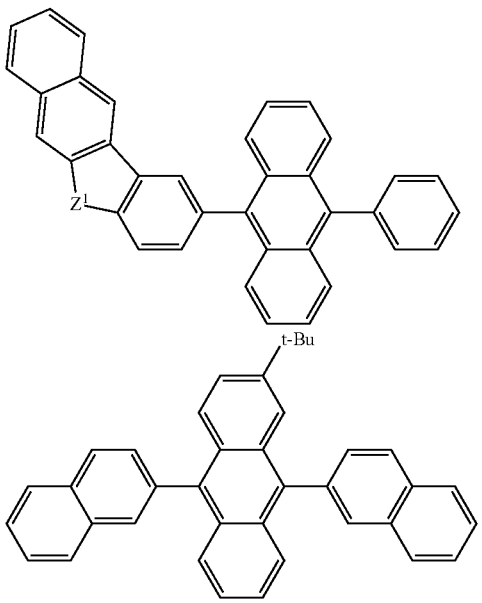

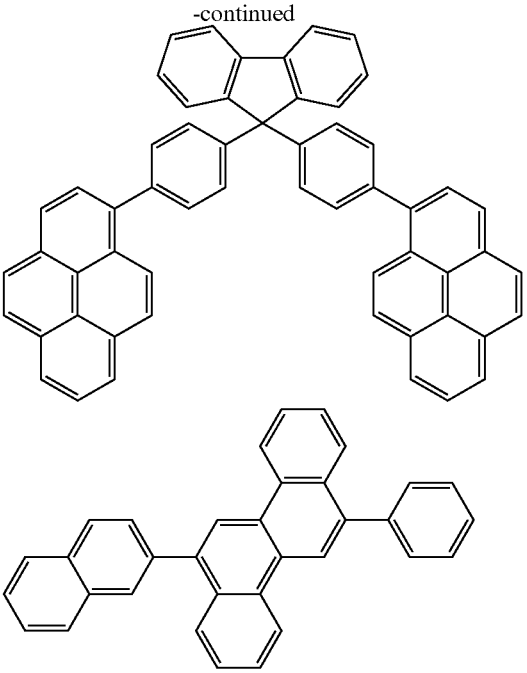

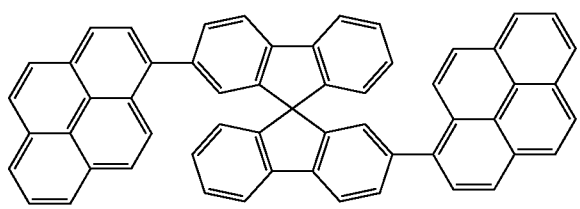

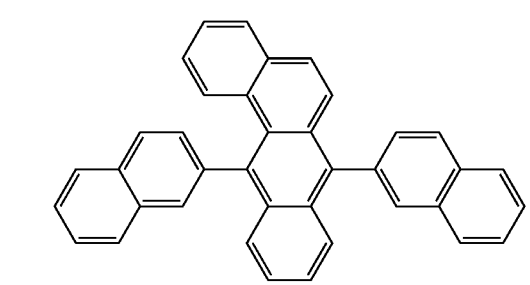

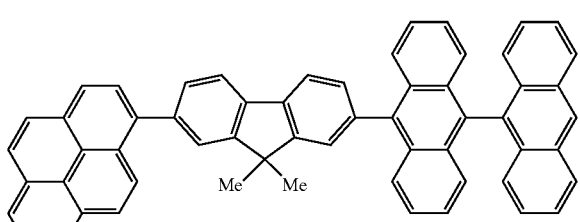

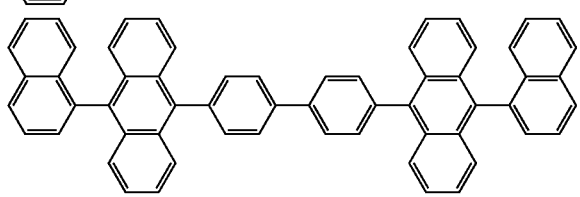

(Polymer Host Material)

The polymer host material has a polystyrene-equivalent number-average molecular weight of preferably $5\times10^3$ to $1\times10^6$, more preferably $1\times10^4$ to $5\times10^5$, and further preferably $2\times10^4$ to $2\times10^5$. The polymer host material has a polystyrene-equivalent weight-average molecular weight of preferably $1\times10^4$ to $2\times10^6$, more preferably $2\times10^4$ to $1\times10^6$, and further preferably $5\times10^4$ to $5\times10^5$.

The polymer host material may be any of a block copolymer, a random copolymer, an alternative copolymer and a graft copolymer, and may also be another form, and it is preferably a copolymer obtained by copolymerizing a plurality of raw material monomers.

It is preferable that the polymer host material contains a condensed ring skeleton in which only three or more benzene rings are condensed as a group obtained by removing from an aromatic hydrocarbon having a condensed ring skeleton in which only three or more benzene rings are condensed one or more hydrogen atoms bonding directly to carbon atoms constituting the condensed ring skeleton (the condensed ring-containing aromatic hydrocarbon group), and this group optionally has a substituent.

The polymer host material preferably contains a condensed ring-containing aromatic hydrocarbon group in the main chain of the polymer compound, more preferably contains a group obtained by removing from an aromatic hydrocarbon having a condensed ring skeleton in which only three or more benzene rings are condensed two hydrogen atoms bonding directly to carbon atoms constituting the condensed ring skeleton (divalent condensed ring-containing aromatic hydrocarbon group) in the main chain of the polymer compound, since the initial degradation of the light emitting device of the present embodiment is more suppressed. This group optionally has a substituent.

In the polymer host material, the condensed ring-containing aromatic hydrocarbon group is preferably a group obtained by removing from a compound represented by the formula (FH) one or more (preferably 5 or less, more preferably 1 to 3, and further preferably 2) hydrogen atoms, since the initial degradation of the light emitting device of the present embodiment is more suppressed.

In the polymer host material, the content of the condensed ring-containing aromatic hydrocarbon group contained in the polymer compound is usually 0.1% by mol to 100% by mol with respect to the total content of all constitutional units contained in the polymer compound, and since the initial degradation of the light emitting device of the present embodiment is more suppressed, it is preferably 1% by mol to 100% by mol, more preferably 10% by mol to 100% by mol, and further preferably 30% by mol to 100% by mol.

The polymer host material may contain only one type of the condensed ring-containing aromatic hydrocarbon group, and may contain two or more types, and since synthesis of the polymer host material is easy, it may contain preferably 1 to 5 types of the groups, more preferably 1 to 3 types of the groups, and further preferably 1 type of the group.

In the polymer host material, the examples and preferable ranges of the substituent which the condensed ring-containing aromatic hydrocarbon group optionally has are the same as the examples and preferable ranges of the substituent which the condensed ring-containing aromatic hydrocarbon optionally has.

The polymer host material may contain a constitutional unit other than the condensed ring-containing aromatic hydrocarbon group in the polymer compound, preferably contains a constitutional unit other than the condensed ring-containing aromatic hydrocarbon group in the polymer compound.

The constitutional unit other than the condensed ring-containing aromatic hydrocarbon group includes, for example, groups obtained by removing from an aromatic hydrocarbon group (preferably an arylene group), a heterocyclic group (preferably a divalent heterocyclic group) and an aromatic amine compound other than the condensed ring-containing aromatic hydrocarbon group one or more hydrogen atoms (preferably two hydrogen atoms), and the foregoing groups optionally have a substituent. The examples and preferable ranges of this substituent are the same as the examples and preferable ranges of the substituent which the condensed ring-containing aromatic hydrocarbon optionally has.

In the polymer host material, the total content of the condensed ring-containing aromatic hydrocarbon group and the group obtained by removing from an aromatic hydrocarbon group, a heterocyclic group and an aromatic amine compound other than the condensed ring-containing aromatic hydrocarbon group one or more hydrogen atoms, contained in the polymer compound, is usually 1% by mol to 100% by mol with respect to the total content of all constitutional units contained in the polymer compound, and since the initial degradation of the light emitting device of the present embodiment is more suppressed, it is preferably 50% by mol to 100% by mol, and more preferably 70% by mol to 100% by mol.

The polymer host material may contain only one type of the constitutional unit or may contain two or more types of the constitutional units other than the condensed ring-containing aromatic hydrocarbon group, in the polymer compound.

<Guest Material>

The aromatic amine compound denotes a compound containing a skeleton in which at least one of an amino group and a substituted amino group is substituted in an aromatic hydrocarbon group or an aromatic heterocyclic group (hereinafter, referred to also as "aromatic amine skeleton"). The aromatic amine skeleton is preferably a skeleton in which one or more substituted amino groups are substituted in an aromatic hydrocarbon group or an aromatic heterocyclic group, more preferably a skeleton in which one or more substituted amino groups are substituted in an aromatic hydrocarbon group, since the initial degradation of the light emitting device of the present embodiment is more suppressed.

The examples and preferable range of the substituted amino group in an aromatic amine compound are the same as the examples and preferable range of the substituted amino group as the substituent which the condensed ring-containing aromatic hydrocarbon optionally has.

The aromatic amine compound may contain only one type of the substituted amino group or may contain two or more types of the substituted amino groups, in the compound. Further, the aromatic amine compound may contain only one of an amino group and a substituted amino group, or may contain only one amino group and one substituted amino group, or may contain two or more amino groups and two or more substituted amino groups, in the compound.

The aromatic amine compound may contain only one type of the aromatic amine skeleton or may contain two or more types of the aromatic amine skeletons, in the compound. Further, the aromatic amine compound may contain only one aromatic amine skeleton, or may contain two or more aromatic amine skeletons, in the compound.

In the aromatic amine skeleton, the number of amino groups substituted on an aromatic hydrocarbon group or an aromatic heterocyclic group is usually from 0 to 10, preferably from 0 to 5, more preferably 0 to 3, and further preferably 0.

In the aromatic amine skeleton, the number of substituted amino groups substituted on an aromatic hydrocarbon group or an aromatic heterocyclic group is usually 1 to 10, and since the initial deterioration of the light emitting device of this embodiment is more suppressed, the number is preferably 1 to 7, more preferably 1 to 5, further preferably 1 to 3.

In the aromatic amine skeleton, the total number of an amino group and a substituted amino group substituted on an aromatic hydrocarbon group or an aromatic heterocyclic group is usually 1 to 10, and since the initial deterioration of the light emitting device of the present embodiment is more suppressed, the total number is preferably 1 to 7, more preferably 1 to 5, further preferably 1 to 3.

In the aromatic amine compound, the aromatic hydrocarbon group is preferably a group obtained by removing from a mono-cyclic or bi-cyclic to hexa-cyclic aromatic hydrocarbon one or more hydrogen atoms bonding directly to carbon atoms constituting the ring, more preferably a group obtained by removing from a tri-cyclic to penta-cyclic aromatic hydrocarbon one or more hydrogen atoms bonding directly to carbon atoms constituting the ring, further preferably a group obtained by removing from anthracene, phenanthrene, fluorene, benzoanthracene, benzophenanthrene, benzofluorene or pyrene one or more hydrogen atoms bonding directly to carbon atoms constituting the ring, particularly preferably a group obtained by removing from benzoanthracene, benzophenanthrene or pyrene one or more hydrogen atoms bonding directly to carbon atoms constituting the ring, since the initial degradation of the light emitting device of the present embodiment is more suppressed, and the foregoing groups optionally have a substituent.

In the aromatic amine compound, the aromatic heterocyclic group includes, for example, groups obtained by removing from a mono-cyclic or bi-cyclic to hepta-cyclic aromatic heterocyclic compound among heterocyclic compounds exemplified in the section of the heterocyclic group described above one or more hydrogen atoms bonding directly to atoms constituting the ring, and is preferably a group obtained by removing from a mono-cyclic or bi-cyclic to hexa-cyclic aromatic heterocyclic compound one or more hydrogen atoms bonding directly to atoms constituting the ring, more preferably a group obtained by removing form a tri-cyclic to penta-cyclic aromatic heterocyclic compound one or more hydrogen atoms bonding directly to atoms constituting the ring, further preferably a group obtained by removing from dibenzofuran, dibenzothiophene, carbazole, azaanthracene, diazaanthracene, azaphenanthrene, diazaphenanthrene, benzocarbazole, benzonaphthofuran or benzonaphthothiophene one or more hydrogen atoms bonding directly to atoms constituting the ring, and the foregoing groups optionally have a substituent.

In the aromatic amine compound, the substituent which the aromatic hydrocarbon group and the aromatic heterocyclic group optionally have is a substituent other than an amino group and a substituted amino group, and is preferably a halogen atom, an alkyl group, a cycloalkyl group, an alkoxy group, a cycloalkoxy group, an aryl group or a monovalent heterocyclic group, more preferably an alkyl group, a cycloalkyl group, an aryl group or a monovalent heterocyclic group, further preferably an alkyl group or a cycloalkyl group, and the foregoing groups optionally further have a substituent.

In the aromatic amine compound, the examples and preferable ranges of the aryl group and the monovalent heterocyclic group as the substituent which an aromatic hydrocarbon group and an aromatic heterocyclic group optionally have are the same as the examples and preferable ranges of the aryl group and the monovalent heterocyclic group as the substituent which an aromatic hydrocarbon in which only three or more benzene rings are condensed optionally has, respectively.

In the aromatic amine compound, the examples and preferable ranges of the substituent which the substituent which an aromatic hydrocarbon group and an aromatic heterocyclic group optionally have optionally further has are the same as the examples and preferable ranges of the substituent which the substituent which an aromatic hydrocarbon in which only three or more benzene rings are condensed optionally has optionally further has.

The guest material may further contain a compound other than the aromatic amine compound, however, since the initial deterioration of the light emitting device of this embodiment is more suppressed, it is preferable that the guest material contains an aromatic amine compound as the main component. The content ratio of the aromatic amine compound in the guest material may be, for example, 10% by mass or more, and since the initial deterioration of the light emitting device of this embodiment is more suppressed, it is preferably 30% mass or more, more preferably 50% by mass or more, further preferably 70% by mass or more, particularly preferably 90% by mass or more, especially preferably 95% by mass or more, and it may also be 100% by mass.

The guest material may contain only one type of the aromatic amine compound or may contain two or more types of the aromatic amine compounds. When the guest material further contains a compound other than the aromatic amine compound, the guest material may contain only one type or may contain two or more types of the compounds other than the aromatic amine compound.

The aromatic amine compound may be a polymer compound (hereinafter, referred to also as "polymer guest material") or may be a low molecular compound (hereinafter, referred to also as "low molecular guest material"), and the low molecular quest material is preferable.
(Low Molecular Guest Material)

The molecular weight of the low molecular guest material is usually $1 \times 10^2$ to $1 \times 10^4$, preferably $2 \times 10^2$ to $5 \times 10^3$, more preferably $3 \times 10^2$ to $2 \times 10^3$, and further preferably $4 \times 10^2$ to $1 \times 10^3$.

The total number of amino groups and substituted amino groups contained in the low molecular guest material is usually 1 to 20, and since the initial deterioration of the light emitting device of this embodiment is more suppressed, the number is preferably 1 to 15, more preferably 1 to 10, further preferably 1 to 5, and particularly preferably 1 to 3.

The total number of amino groups contained in the low molecular guest material is usually 0 to 10, preferably 0 to 5, more preferably 0 to 3, and further preferably 0.

The total number of substituted amino groups contained in the low molecular guest material is usually 1 to 20, and since the initial deterioration of the light emitting device of the present embodiment is more suppressed, it is preferably 1 to 15, more preferably 1 to 10, further preferably 1 to 5, and particularly preferably 1 to 3.

The low molecular guest material may contain only one type of the substituted amino group or two or more types of the substituted amino groups, however, since synthesis of the low molecular host material is easy, one to ten types are preferable, one to five types are more preferable, one to three types are further preferable, and one type is particularly preferable.

The total number of aromatic amine skeletons contained in the low molecular guest material is usually from 1 to 10, and since the initial deterioration of the light emitting device of this embodiment is more suppressed, it is preferably from 1 to 7, more preferably 1 to 5, further preferably 1 to 3, and particularly preferably 1.

The low molecular guest material may contain only one type of the aromatic amine skeleton or two or more types of the aromatic amine skeletons, however, since synthesis of the low molecular host material is easy, 1 to 5 types are preferable, 1 to 3 types are more preferable, and 1 type is further preferable.
[Compound Represented by the Formula (FB)]

The low molecular guest material is preferably a compound represented by the formula (FB), since the initial degradation of the light emitting device of the present embodiment is more suppressed.

$n^{1H}$ is usually an integer of 1 or more and 10 or less, and since synthesis of a compound represented by the formula (FB) is easy, it is preferably an integer of 1 or more and 7 or less, more preferably an integer of 1 or more and 5 or less, and further preferably an integer of 1 or more and 3 or less.

$Ar^{1B}$ is preferably an aromatic hydrocarbon group optionally having a substituent, since the initial deterioration of the light emitting device of this embodiment is more suppressed.

The examples and preferable ranges of the aromatic hydrocarbon group and the aromatic heterocyclic group for $Ar^{1B}$ are the same as the examples and preferable ranges of the aromatic hydrocarbon group and the aromatic heterocyclic group in the aromatic amine compound, respectively.

The examples and preferable ranges of the substituent which $Ar^{1B}$ optionally has are the same as the examples and preferable ranges of the substituent which the aromatic hydrocarbon group and the aromatic heterocyclic group optionally have, in the aromatic amine compound.

$R^{1B}$ is preferably a substituted amino group since the initial deterioration of the light emitting device of the present embodiment is more suppressed, and this group optionally further has a substituent.

The examples and preferable ranges of the substituted amino group for $R^{1B}$ are the same as the examples and preferable ranges of the substituted amino group in the aromatic amine compound.

The examples and preferable ranges of the substituent which $R^{1B}$ optionally has are the same as the examples and preferable ranges of the substituent which the substituent which the aromatic hydrocarbon group and the aromatic heterocyclic group optionally have optionally further has, in the aromatic amine compound.

Examples of the low molecular guest material include compounds represented by the following formula and compounds described in Examples. These compounds optionally have a substituent. In the formula, $Z^1$ has the same meaning as described above.

[Chemical Formula 7]

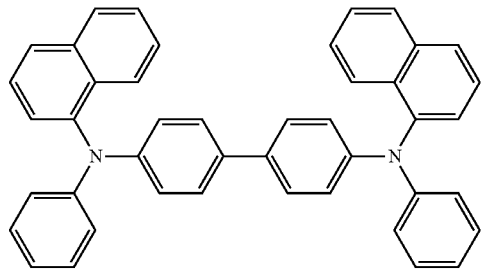
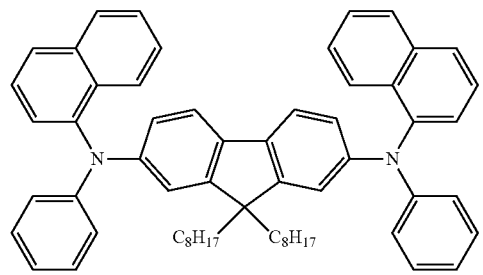
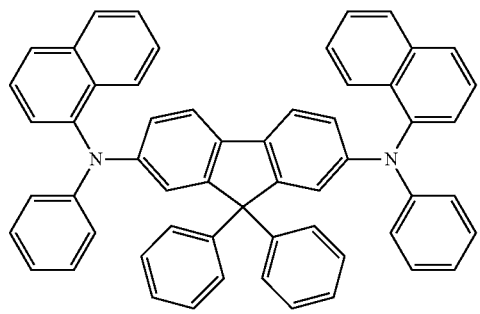
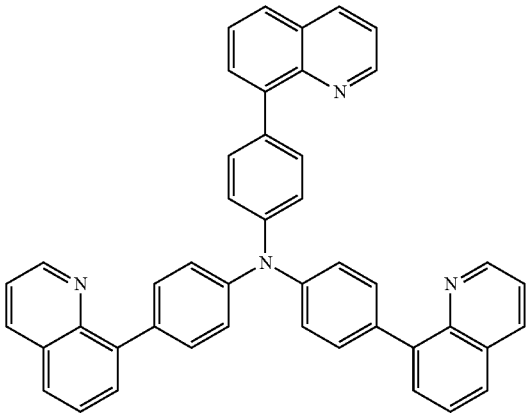
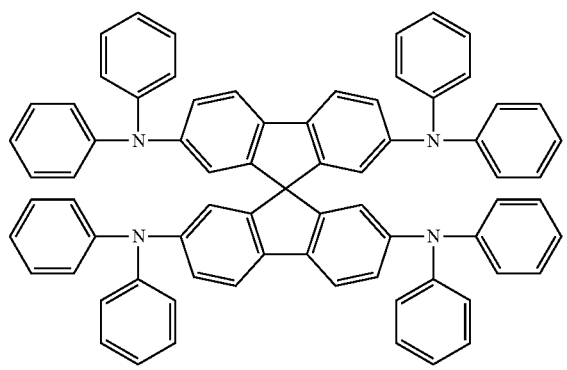
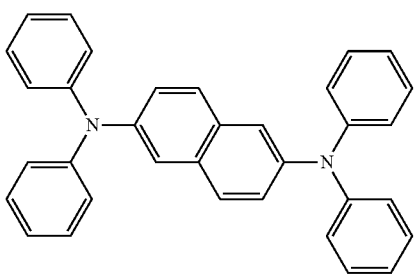

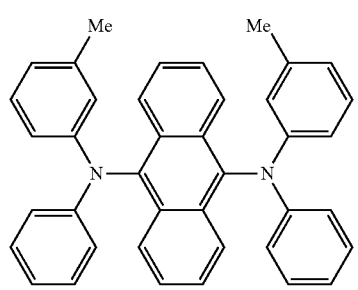
[Chemical Formula 8]
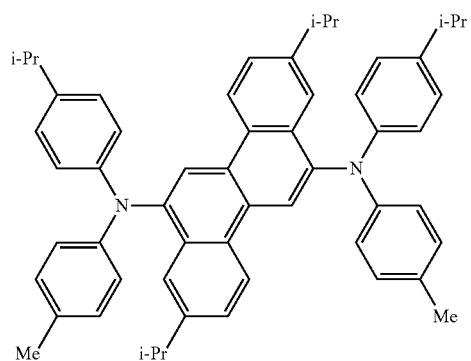
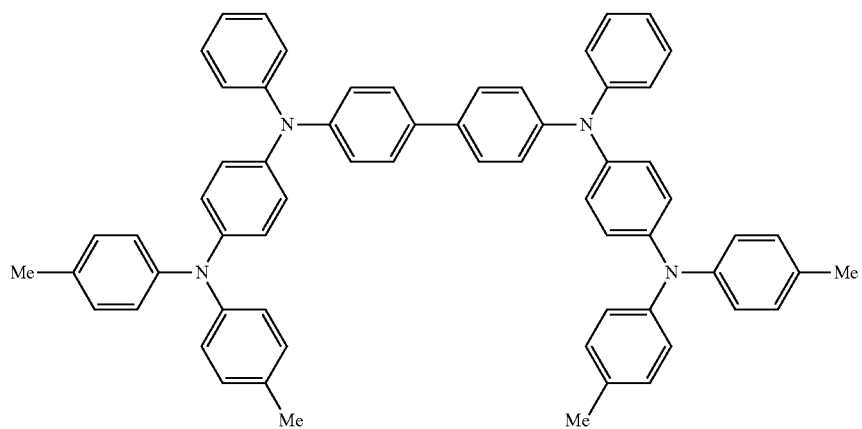
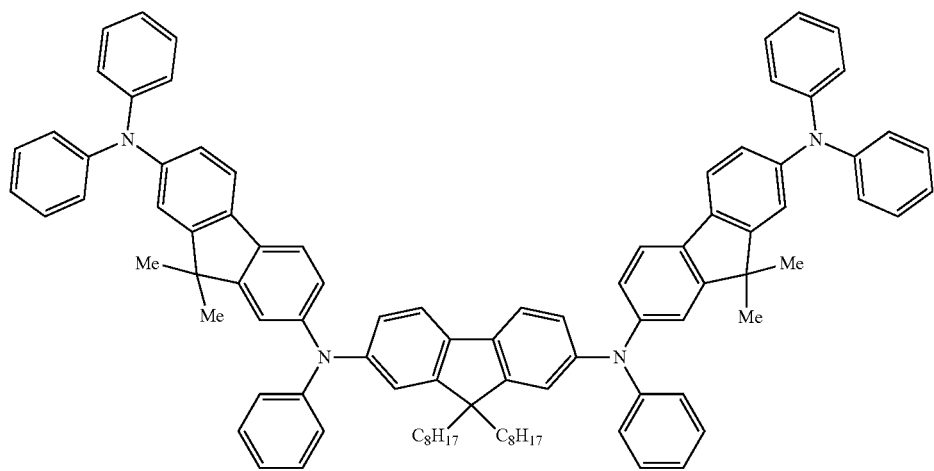

-continued
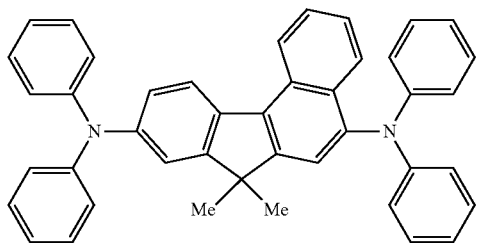
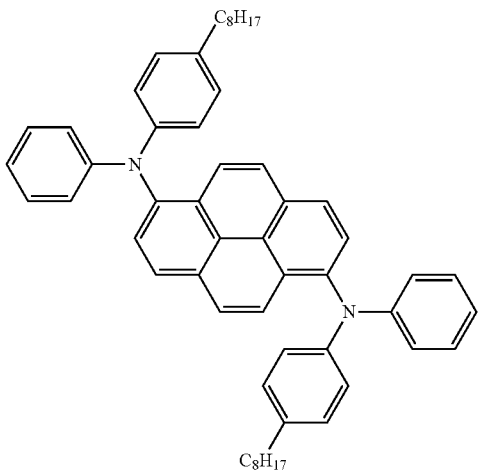
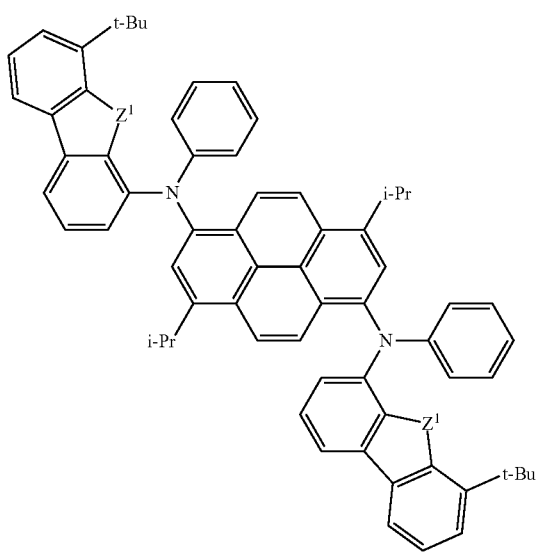
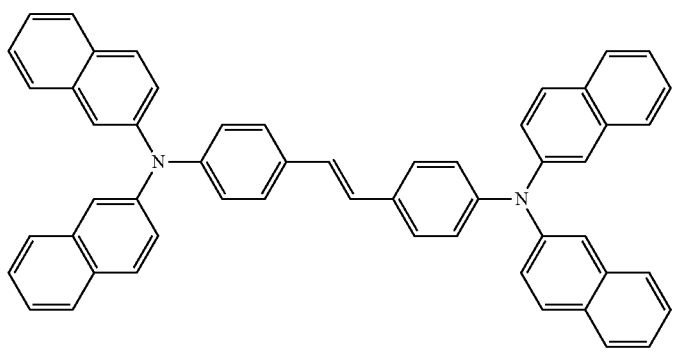
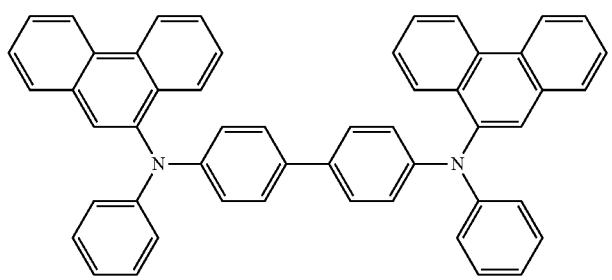

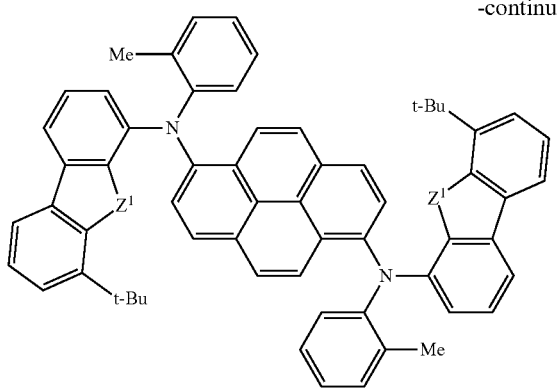

(Polymer Guest Material)

The preferable ranges of the number average molecular weight and the weight average molecular weight in terms of polystyrene of the polymer guest material are the same as the preferable ranges of the number average molecular weight and the weight average molecular weight in terms of polystyrene of the polymer host material, respectively.

The polymer guest material may be any of a block copolymer, a random copolymer, an alternating copolymer and a graft copolymer, or may be another form, and a copolymer obtained by copolymerizing a plurality of raw material monomers is preferable.

The polymer guest material can be referred to as a polymer compound containing a constitutional unit having an aromatic amine skeleton. The polymer guest material preferably contains an aromatic amine skeleton in the main chain of the polymer compound, since the initial deterioration of the light emitting device of this embodiment is more suppressed.

In the polymer guest material, the aromatic amine skeleton is preferably a group obtained by removing from a compound represented by the formula (FB) one or more hydrogen atoms (preferably five or less, more preferably 1 to 3, further preferably 2 hydrogen atoms), since the initial deterioration of the light emitting device of the present embodiment is more suppressed.

In the polymer guest material, the content of the aromatic amine skeleton contained in the polymer compound is usually 0.1% by mol to 100% by mol based on the total content of all constitutional units contained in the polymer compound, and since the initial deterioration of the light emitting device of this embodiment is more suppressed, it is preferably 1% by mol to 100% by mol, more preferably 5% by mol to 100% by mol, and further preferably 10% by mol to 100% by mol.

In the polymer guest material, the polymer compound may contain only one type of the aromatic amine skeleton or may contain two or more types of the aromatic amine skeletons, and since synthesis of the polymer guest material is easy, one to five types are preferable, one to three types are more preferable, and one type is further preferable.

In the polymer guest material, the examples and preferable ranges of the substituent which the aromatic amine skeleton optionally has are the same as the examples and preferable ranges of the substituent which the aromatic hydrocarbon group and the aromatic heterocyclic group optionally have, in the aromatic amine compound.

In the polymer guest material, the polymer compound may contain a constitutional unit other than the aromatic amine skeleton, and it is preferable that a constitutional unit other than the aromatic amine skeleton is contained in the main chain of the polymer compound.

Examples of the constitutional unit other than the aromatic amine skeleton include aromatic hydrocarbon groups (preferably an arylene group) and heterocyclic groups (preferably a divalent heterocyclic group), and the foregoing groups optionally have a substituent. The examples and preferable ranges of the substituent are the same as the examples and preferable ranges of the substituent which the condensed ring-containing aromatic hydrocarbon optionally has.

In the polymer guest material, the total content of the aromatic amine skeleton, the aromatic hydrocarbon group and the heterocyclic group contained in the polymer compound is usually 1% by mol to 100% by mol based on the total content of all the constitutional units contained in the polymer compound, and since the initial deterioration of the light emitting device of the present embodiment is more suppressed, it is preferably 50% by mol to 100% by mol, and more preferably 70% by mol. 100% by mol.

In the polymer guest material, the polymer compound may contain only one type of the constitutional unit or may contain two or more types of the constitutional units other than the aromatic amine skeleton.

<Amount ($C^1$) of Silicon Atom Contained in Guest Material>

In the composition for light emitting device of the present embodiment, the amount ($C^1$) of a silicon atom contained in the guest material is usually 750 ppm by mass or less based on the total amount of the guest material. In the present specification, the phrase "the amount of a silicon atom contained in the guest material" does not mean that the guest material contains a silicon atom, and the guest material may or may not contain a silicon atom. In the guest material of the present embodiment, the amount of a silicon atom is preferably 75 ppm by mass or less, more preferably 7.5 ppm by mass or less, further preferably 5 ppm by mass or less, particularly preferably 3 ppm by mass or less, especially preferably 1 ppm by mass or less, particularly more preferably 0.5 ppm by mass or less, especially more preferably 0.1 ppm by mass or less, especially particularly preferably 0 ppm by mass, since the initial deterioration of the light emitting device of this embodiment is more suppressed.

The amount ($C^1$) of a silicon atom contained in the guest material of the present embodiment is such that when one type of the guest material of the present embodiment is used, the amount of a silicon atom in the one type of the guest material is regarded as $C^1$, and when the guest material of the present embodiment is composed of a plurality types of compounds having different amounts of a silicon atom, $C^1$ is calculated according to the amounts of a silicon atom in the plurality types of the compounds and the mass ratio of each compound. A specific method of calculating $C^1$ will be described using examples D1 and D2 described later.

First, in Example D1, the amount of a silicon atom in the compound EM2 measured by ICP emission spectroscopy is below the detection limit, thus, $C^1$ is 0 ppm by mass.

Next, in Example D2, the amounts of a silicon atom in the compound EM1 and the compound EM2 measured by ICP emission spectroscopy are 8 ppm by mass and below the detection limit (that is, 0 ppm by mass), respectively. The mass ratio between the compound EM1 and the compound EM2 is compound EM1:compound EM2=3:7.

Therefore, $C^1$ in Example D2 can be determined from the amounts of a silicon atom contained in the compound EM2 and the compound EM2 and the charging amounts thereof, and is determined as follows.

$$C^1=\{8\times3/(3+7)\}+\{0\times7/(3+7)\}=2.4 \text{ ppm by mass}$$

In the same manner, $C^1$ in Example D3 is 0 ppm by mass.

<Amount ($C^H$) of Silicon Atom Contained in Host Material>

In the composition for light emitting device of the present embodiment, the amount ($C^H$) of a silicon atom contained in the host material is usually 2000 ppm by mass or less based on the total amount of the host material. In the present specification, the phrase "amount of a silicon atom contained in the host material" does not mean that the host material contains a silicon atom, and the host material may or may not contain a silicon atom. In the host material of the present embodiment, the amount of a silicon atom is preferably 200 ppm by mass or less, more preferably 20 ppm by mass or less, further preferably 10 ppm by mass or less, particularly preferably 5 ppm by mass or less, more particularly preferably 1 ppm by mass or less, especially preferably 0.5 ppm by mass or less, more especially preferably 0.1 ppm by mass or less, and still particularly preferably 0 ppm by mass, since the initial deterioration of the light emitting device of the present embodiment is more suppressed.

The specific calculation method of $C^H$ can be obtained in the same manner as the specific calculation method of $C^1$ described above.

For example, in Example D1, $C^H$ is 0 ppm by mass. In Example D2, $C^H$ is 0 ppm by mass. In Example D3, $C^H$ is 0.53 ppm by mass.

<Method for reducing $C^1$ and $C^H$>

As a method for reducing $C^1$ and $C^H$, for example, purification can be mentioned.

The purification includes known purification methods described in the 4th edition Experimental chemistry course (1993, Maruzen Co., Ltd.), the 5th edition Experimental chemistry course (2007, Maruzen Co., Ltd.), New experimental chemistry course (1975, Maruzen Co., Ltd.), Guidance of organic chemistry experiment (1988, Kagakudojin Publishing) and the like.

Purification includes, for example, sublimation, extraction, reprecipitation, recrystallization, chromatography, and adsorption.

The purification of the low molecular quest material and the low molecular host material is preferably sublimation, recrystallization, chromatography or adsorption, more preferably sublimation or recrystallization, further preferably sublimation, since the amount of a silicon atom can be further reduced.

The purification of the polymer guest material and the polymer host material is preferably reprecipitation, chromatography or adsorption because the amount of a silicon atom can be further reduced.

When purification is performed twice or more, those methods may be the same or different.

In sublimation, the degree of vacuum and the sublimation temperature may be appropriately set according to the material to be sublimated. The degree of vacuum is preferably $1\times10^{-10}$ Pa to $1\times10^5$ Pa, more preferably $1\times10^{-7}$ Pa to $1\times10^2$ Pa, further preferably $1\times10^{-5}$ Pa to 1 Pa, and particularly preferably $1\times10^{-4}$ Pa to $1\times10^{-2}$ Pa. Further, the sublimation temperature is preferably $-100°$ C. to $1000°$ C., more preferably $0°$ C. to $700°$ C., further preferably $100°$ C. to $500°$ C., and particularly preferably $200°$ C. to $350°$ C.

The extraction is preferably separating or solid-liquid extraction using a Soxhlet extractor.

The solvent used for the extraction includes, for example, alcohol solvents such as methanol, ethanol, propanol, ethylene glycol, glycerin, 2-methoxyethanol, 2-ethoxyethanol and the like; ether solvents such as diethyl ether, tetrahydrofuran (THF), dioxane, cyclopentyl methyl ether, diglyme and the like; halogen solvents such as methylene chloride, chloroform and the like; nitrile solvents such as acetonitrile, benzonitrile and the like; hydrocarbon solvents such as hexane, decalin, toluene, xylene, mesitylene and the like; amide solvents such as N,N-dimethylformamide, N,N-dimethylacetamide and the like; acetone, dimethyl sulfoxide, and water. The solvent may be used alone or in combination of two or more.

The chromatography is preferably column chromatography.

Silica gel or alumina is preferred as the filler used for column chromatography.

Examples of solvents used for chromatography are the same as the examples of solvents used for extraction.

Examples of the solvent used for reprecipitation and recrystallization are the same as the examples of the solvent used for extraction.

As the adsorption, treatment with an adsorbent is preferable. The adsorbent is preferably activated carbon, silica gel, alumina or Celite.

The treatment with the adsorbent is usually performed in a solvent. Examples of the solvent used for the treatment with the adsorbent are the same as the examples of the solvent used for the extraction.

<Composition for Light Emitting Device>

The composition for light emitting device of the present embodiment contains a host material and a quest material.

In the composition for light emitting device of the present embodiment, the host material and the quest material each may be contained singly or in combination of two or more, respectively.

In the composition for light emitting device of the present embodiment, the maximum peak wavelength of the emission spectrum of the host material at room temperature is preferably shorter than the maximum peak wavelength of the emission spectrum of the guest material at room temperature.

In the composition for light emitting device of this embodiment, the maximum peak wavelength of the emission spectrum of the host material at room temperature is preferably 300 nm or more and 500 nm or less, more preferably 330 nm or more and 480 nm or less, and further preferably 360 nm or more and 460 nm or less.

In the composition for light emitting device of this embodiment, the maximum peak wavelength of the emission spectrum of the guest material at room temperature is preferably 380 nm or more and 500 nm or less, more preferably 400 nm or more and 490 nm or less, and further preferably 430 nm or more and 480 nm or less.

The maximum peak wavelength of the emission spectrum of the host material and the quest material can be evaluated by dissolving the measurement object in an organic solvent such as xylene, toluene, chloroform or tetrahydrofuran to prepare a dilute solution ($1\times10^{-6}$% by mass to $1\times10^{-3}$% by mass), and measuring the PL spectrum of the diluted solution at room temperature. As the organic solvent for dissolving the measurement object, toluene or xylene is preferable.

In the composition for light emitting device of the present embodiment, the total amount of a silicon atom contained in the host material and a silicon atom contained in the guest material is 20 ppm by mass or less with respect to the total amount of the host material and the guest material, and since the initial deterioration of the light emitting device of the embodiment is suppressed, it is preferably 18 ppm by mass or less, more preferably 10 ppm by mass or less, further preferably 5 ppm by mass or less, particularly preferably 3 ppm by mass or less, especially particularly preferably 1 ppm by mass or less, still particularly preferably 0.5 ppm by mass or less, still more particularly preferably 0.1 ppm by mass or less, and particularly preferably 0 ppm by mass. In addition, the total amount of a silicon atom contained in the host material and a silicon atom contained in the guest material, in the composition for light emitting device of the present embodiment, is preferably 0.001 ppm by mass or more, more preferably 0.005 ppm by mass or more, further preferably 0.01 ppm by mass or more, particularly preferably 0.05 ppm by mass or more, especially preferably 0.1 ppm by mass or more, particularly preferably 0.2 ppm by mass or more, particularly further preferably 0.5 ppm by mass or more, and especially particularly preferably 0.7 ppm by mass or more, with respect to the total amount of the host material and the guest material, since the initial deterioration of the light emitting device of the present embodiment can be controlled.

In the present embodiment, the reason why the initial deterioration of the light emitting device is suppressed is considered as follows.

The aromatic compound contained as a host material in the composition for light emitting device of this embodiment has a condensed ring skeleton in which only three or more benzene rings are condensed. The present inventors believe that such a condensed ring skeleton electrically interacts with an aromatic amine compound contained in the guest compound. On the other hand, the present inventors believe that the aromatic amine compound contained as a guest material in the composition for light emitting device of this embodiment electrically interacts with the aromatic compound contained as a host material. Then, the present inventors believe that, in the composition for light emitting device of the present embodiment, when the total amount of a silicon atom contained in the host material and a silicon atom contained in the guest material exceeds a predetermined amount, a silicon atom exerts an adverse effect on the above-described interaction. Then, it is considered that this adverse effect causes a decrease in the light emission characteristics, charge transport characteristics or charge injection characteristics of the composition for light emitting device of the present embodiment, or disrupts the balance of the charges of the light emitting device of the present embodiment, leading to the initial deterioration of the light emitting device of the present embodiment.

Hence, based on the above-described idea, the present inventors believe that, since the total amount of a silicon atom contained in the host material and a silicon atom contained in the guest material is in a specific range, the effect by a silicon atom described above is suppressed, and the effect of suppressing the initial deterioration of the light emitting device is obtained, in the present embodiment.

The total amount (ppm by mass) of a silicon atom contained in the host material and a silicon atom contained in the guest material is expressed by $C^H W^H + C^1 W^1$, the ratio of the mass of the host material to the total mass of the host material and the guest material being WEI and the ratio of the mass of the guest material to the total mass of the host material and the guest material being $W^1$.

$W^H$ is usually 0.01 to 0.9999, and since the initial deterioration of the light emitting device of this embodiment is more suppressed, it is preferably 0.30 to 0.999, more preferably 0.50 to 0.995, further preferably 0.70 to 0.99, and particularly preferably 0.85 to 0.95.

$W^1$ is usually 0.0001 to 0.99, and since the initial deterioration of the light emitting device of the present embodiment is more suppressed, it is preferably 0.001 to 0.70, more preferably 0.005 to 0.50, further preferably 0.01 to 0.30, and particularly preferably 0.05 to 0.15.

The specific method for calculating $W^H$ and $W^1$ will be illustrated using Example D1 and Example D2 described later.

First, in Example D1, the mass ratio of a compound H2 (host material) and a compound EM2 (guest material) is compound H2:compound EM2=90:10.

That is, $W^H$ and $W^1$ in Example D1 can be determined from the charging amounts, and determined as follows.

$$W^H = 90/(90+10) = 0.90$$

$$W^1 = 10/(90+10) = 0.10$$

In Example D2, the mass ratio of a compound H2, compound EM1 and a compound EM2 is compound H2:compound EM1:compound EM2=90:3:7.

That is, $W^H$ and $W^1$ in Example D2 can be determined from the charging amounts, and determined as follows.

$$W^H = 90/(90+3+7) = 0.90$$

$$W^1 = (3+7)/(90+3+7) = 0.10$$

In the same manner, $W^H$ and $W^1$ in Example D3 are determined as described below.

$$W^H = (2+88)/(2+88+10) = 0.90$$

$$W^1 = 10/(2+88+10) = 0.10$$

As described above, $C^H W^H + C^1 W^1$ can be calculated by calculating $C^1$, $C^H$, $W^1$ and $W^H$.

For example, $C^H W^H + C^1 W^1$ in Example D1 is determined as described below.

$$C^H W^H + C^1 W^1 = (0 \times 0.90) + (0 \times 0.10) = 0 \text{ ppm by mass}$$

For example, $C^H W^H + C^1 W^1$ in Example D2 is determined as follows.

$$C^H W^H + C^1 W^1 = (0 \times 0.90) + (2.4 \times 0.10) = 0.24 \text{ ppm by mass}$$

For example, $C^H W^H + C^1 W^1$ in Example D3 is determined as follows.

$$C^H W^H + C^1 W^1 = (0.53 \times 0.90) + (0 \times 0.10) = 0.48 \text{ ppm by mass}$$

$C^H W^H + C^1 W^1$ is usually 20 ppm by mass or less, and since the initial degradation of the light emitting device of the present embodiment is suppressed, it is preferably 18 ppm by mass or less, more preferably 10 ppm by mass or less, further preferably 5 ppm by mass or less, particularly preferably 3 ppm by mass or less, especially preferably 1 ppm by mass or less, especially more preferably 0.5 ppm by mass or less, especially further preferably 0.1 ppm by mass or less, and especially particularly preferably 0 ppm by mass. Further, $C^H W^H + C^1 W^1$ is preferably 0.001 ppm by mass or more, more preferably 0.005 ppm by mass or more, further preferably 0.01 ppm by mass or more, particularly preferably 0.05 ppm by mass or more, especially preferably 0.1 ppm by mass or more, especially more preferably 0.2 ppm by mass or more, especially further preferably 0.5 ppm by mass or more, and especially particularly preferably 0.7 ppm by mass or more, since the initial degradation of the light emitting device of the present embodiment can be controlled.

(Other Component)

The composition for light emitting device of the present embodiment may be a composition containing at least one material selected from the group consisting of a host material, a guest material, a hole transporting material, a hole injection material, an electron transporting material, an electron injection material, a light emitting material, an antioxidant, and a solvent. However, the hole transporting material, the hole injection material, the electron transporting material, the electron injection material, and the light emitting material are different from the host material and the guest material.

When the composition for light emitting device of the present embodiment further contains at least one selected from the group consisting of a hole transporting material, a hole injection material, an electron transporting material, an electron injection material, a light emitting material, an antioxidant and a solvent, it is preferable to reduce the amount of a silicon atom contained therein by the above-described purification.

[Ink]

The composition containing the host material the quest material and a solvent (hereinafter, referred to as "ink") is suitable for fabrication of a light emitting device using a wet method such as a spin coating method, a casting method, a micro gravure coat method, a gravure coat method, a bar coating method, a roll coating method, a wire bar coating method, a dip coating method, a spray coating method, a screen printing method, a Flexographic printing method, an offset printing method, an inkjet printing method, a capillary coating method, a nozzle coating method and the like. The viscosity of the ink may be adjusted according to the type of the printing method, and is preferably 1 mPa·s to 20 mPa·s at 25° C.

The solvent contained in the ink is preferably a solvent capable of dissolving or uniformly dispersing solid components in the ink. The solvent includes, for example, chlorine solvents, ether solvents, aromatic hydrocarbon solvents, aliphatic hydrocarbon solvents, ketone solvents, ester solvents, polyhydric alcohol solvents, alcohol solvents, sulfoxide solvents and amide solvents.

In the ink, the compounding amount of the solvent is usually 1000 to 100000 parts by mass, when the sum of the host material and the guest material is taken as 100 parts by mass.

The solvent may be used singly or in combination of two or more kinds thereof.

[Hole Transporting Material]

The hole transporting material is classified into a low molecular compound and a polymer compound, and is preferably a polymer compound having a crosslinkable group.

Examples of the polymer compound include polyvinyl carbazole and derivatives thereof; polyarylene having an aromatic amine structure in a side chain or a main chain and derivatives thereof. The polymer compound may be a compound to which an electron accepting site such as fullerene, tetrafluorotetracyanoquinodimethane, tetracyanoethylene, and trinitrofluorenone is bonded.

In the composition for light emitting device of the present embodiment, when a hole transporting material is contained, the compounding amount of the hole transporting material is usually 1 part by mass to 400 parts by mass when the sum of the host material and the guest material is taken 100 parts by mass.

The hole transporting material may be used singly or in combination of two or more.

[Electron Transporting Material]

The electron transporting material is classified into a low molecular compound and a polymer compound. The electron transporting material optionally has a crosslinkable group.

The low molecular compound includes, for example, metal complex having 8-hydroxyquinoline as a ligand, oxadiazole, anthraquinodimethane, benzoquinone, naphthoquinone, anthraquinone, tetracyanoanthraquinodimethane, fluorenone, diphenyldicyanoethylene and diphenoquinone, and derivatives thereof.

The polymer compound includes, for example, polyphenylene, polyfluorene, and derivatives thereof. The polymer compound may be doped with a metal.

When the composition for light emitting device of the present embodiment contains an electron transporting material, the compounding amount of the electron transporting material is usually 1 part by mass to 400 parts by mass when the sum of the host material and the guest material is taken as 100 parts by mass.

The electron transporting material may be used singly or in combination of two or more.

[Hole Injection Material and Electron Injection Material]

The hole injection material and the electron injection material are each classified into a low molecular compound and a polymer compound. The hole injection material and the electron injection material optionally have a crosslinkable group.

The low molecular compound includes, for example, metal phthalocyanines such as copper phthalocyanine and the like; carbon; oxides of metals such as molybdenum, tungsten and the like; metal fluorides such as lithium fluoride, sodium fluoride, cesium fluoride, potassium fluoride and the like.

The polymer compound includes, for example, polyaniline, polythiophene, polypyrrole, polyphenylenevinylene, polythienylenevinylene, polyquinoline and polyquinoxaline, and derivatives thereof; electrically conductive polymers such as a polymer containing an aromatic amine structure in the main chain or side chain, and the like.

When the hole-injection material and/or the electron-injection material are contained in the composition for light emitting device of the present embodiment, the compounding amounts of the hole-injection material and the electron-injection material are usually 1 part by mass to 400 parts by mass, respectively, when the sum of the host material and the guest material is taken as 100 parts by mass.

The hole injection material and the electron injection material each may be used alone or in combination of two or more.

(Ion Doping)

When the hole injection material or the electron injection material contains a conductive polymer, the electric conductivity of the conductive polymer is preferably $1\times10^{-5}$ S/cm to $1\times10^{3}$ S/cm. In order to make the electric conductivity of the conductive polymer fall within such a range, the conductive polymer can be doped with an appropriate amount of ions. The type of ions to be doped is an anion for a hole injection material and a cation for an electron injection material. Examples of the anion include a polystyrene sulfonate ion, an alkylbenzene sulfonate ion, and a camphor sulfonate ion. Examples of the cation include a lithium ion, a sodium ion, a potassium ion, and a tetrabutylammonium ion.

The ions to be doped may be used singly or in combination of two or more.

[Light Emitting Material]

The light emitting material is classified into a low molecular compound and a polymer compound. The light emitting material optionally has a crosslinkable group.

The low molecular compound includes, for example, naphthalene and derivatives thereof, anthracene and derivatives thereof, perylene and derivatives thereof, and triplet light emitting complexes containing iridium, platinum or europium as the central metal.

The polymer compound includes polymer compounds containing, for example, an arylene group such as a phenylene group, a naphthalenediyl group, a fluorenediyl group, a phenanthrenediyl group, a dihydrophenanthrenediyl group, an anthracenediyl group, a pyrenediyl group and the like; an aromatic amine residue such as a group obtained by removing from an aromatic amine two hydrogen atoms, and the like; and a divalent heterocyclic group such as a carbazolediyl group, a phenoxazinediyl group, a phenothiazinediyl group and the like.

In the case where the composition for light emitting device of the present embodiment contains a light emitting material, the content of the light emitting material is usually 0.1 part by mass to 400 parts by mass when the sum of the host material and the guest material is taken as 100 parts by mass.

The light emitting material may be used alone or in combination of two or more.

[Antioxidant]

The antioxidant may be any compound that is soluble in the same solvent as for the host material and the guest material and does not inhibit light emission and charge transportation, and examples thereof include a phenolic antioxidant and a phosphorus-based antioxidant.

In the composition for light emitting device of the present embodiment, when an antioxidant is contained, the compounding amount of the antioxidant is usually 0.001 part by mass to 10 parts by mass when the sum of the host material and the guest material is taken as 100 parts by mass.

The antioxidant may be used alone or in combination of two or more.

<Film>

The film contains the composition for light emitting device of the present embodiment, and is suitable as a light emitting layer in a light emitting device. The film can be formed by, for example, a wet method using an ink. In addition, the film can be produced by a dry method such as a vacuum vapor deposition method. Examples of a method for forming a film by a dry method include a method for vapor-depositing the composition for light emitting device of this embodiment and a method for co-evaporating a host material and a quest material.

The thickness of the film is usually from 1 nm to 10 μm.

<Light Emitting Device>

The light emitting device of the present embodiment contains the composition for light emitting device described above.

The configuration of the light emitting device of the present embodiment includes, for example, an anode, a cathode, and an organic layer containing the composition for light emitting device of the present embodiment disposed between the anode and the cathode.

[Layer Constitution]

The layer containing the composition for light emitting device of the present embodiment is usually at least one layer selected from the group consisting of a light emitting layer, a hole transporting layer, a hole injection layer, an electron transporting layer and an electron injection layer. Preferably, it is a light emitting layer. These layers each contain a light emitting material, a hole transporting material, a hole injection material, an electron transporting material, and an electron injection material. Each of these layers can be formed using a light emitting material, a hole-transporting material, a hole injection material, an electron transporting material and an electron injection material by using the same method as for fabricating the above-described film.

The light emitting device has a light emitting layer between an anode and a cathode. The light emitting device of the present embodiment preferably has at least one of a hole injection layer and a hole transporting layer between the anode and the light emitting layer from the standpoint of the hole injectability and the hole transportability, and preferably has at least one of an electron injection layer and an electron transporting layer between the cathode and the light emitting layer from the standpoint of the electron injectability and the electron transportability.

The materials of the hole transporting layer, the electron transporting layer, the light emitting layer, the hole injection layer and the electron injection layer include the above-described hole transporting materials, electron transporting materials, light emitting materials, hole injection materials, electron injection materials and the like, in addition to the composition for the light emitting device of the present embodiment.

If the material for a hole transporting layer, the material for an electron transporting layer and the material for a light emitting layer are soluble in solvents used in forming layers adjacent to the hole transporting layer, the electron transporting layer and the light emitting layer in fabrication of a light emitting device, it is preferable that the materials have a crosslinkable group to avoid dissolution of the materials in the solvents. By forming each layer using the material having a crosslinkable group and cross-linking the crosslinkable group, the layer can be insolubilized.

The method for forming each layer such as a light emitting layer, a hole transporting layer, an electron transporting layer, a hole injection layer, an electron injection layer and the like, in the light emitting device of the present embodiment, includes, for example, a dry method such as vapor deposition from a powder and the like and a wet method such as film formation from a solution or melted state when a low molecular compound is used, and for example, a wet method such as film formation from a solution or melted state and the like when a polymer compound is used. The order, number and thickness of the layers to be laminated are adjusted in consideration of, for example, light emission efficiency and initial deterioration.

[Substrate/Electrode]

The substrate in the light emitting device may advantageously be a substrate on which an electrode can be formed and which does not change chemically in forming an organic layer, and is, for example, a substrate made of a material such as glass, plastic, silicon and the like. When an opaque substrate is used, it is preferable that the electrode farthest from the substrate is transparent or semi-transparent.

The material of the anode includes, for example, electrically conductive metal oxides and semi-transparent metals, preferably includes indium oxide, zinc oxide, tin oxide; electrically conductive compounds such as indium-tin-oxide (ITO), indium-zinc-oxide and the like; argentine-palladium-copper (APC) complex; NESA, gold, platinum, silver and copper.

The material of the cathode includes, for example, metals such as lithium, sodium, potassium, rubidium, cesium, beryllium, magnesium, calcium, strontium, barium, aluminum, zinc, indium and the like; alloys composed of two or more of them; alloys composed of at least one of them and at least one of silver, copper, manganese, titanium, cobalt, nickel, tungsten and tin; and graphite and graphite intercalation compounds. The alloy includes, for example, a magnesium-silver alloy, a magnesium-indium alloy, a magnesium-aluminum alloy, an indium-silver alloy, a lithium-aluminum alloy, a lithium-magnesium alloy, a lithium-indium alloy and a calcium-aluminum alloy.

Each of the anode and the cathode may take a laminated structure composed of two or more layers.

The light emitting device of the present embodiment can be suitably used as a light source for backlight of a liquid crystal display device, a light source for illumination, an organic EL lighting, a display device for computers, televisions and portable terminals (for example, organic EL display and organic EL television).

Although suitable embodiments of the present invention are described above, the present invention is not limited to the above-mentioned embodiments.

For example, one aspect of the present invention may relate to a method for producing a composition for light emitting device in which a host material and a guest material are blended.

<Production Method (1)>

In one aspect, the method for producing a composition for light emitting device may be a production method of a composition for light emitting device, including a host material preparation step of preparing a host material containing a condensed ring-containing aromatic compound, a guest material preparation step of preparing a guest material containing an aromatic amine compound, and a production step of mixing the host material and the guest material at a compounding ratio by which the total amount of a silicon atom contained in the host material and a silicon atom contained in the guest material is 20 ppm by mass or less, to obtain a composition for light emitting device (hereinafter, also referred to as "production method (1)").

In the production method (1), the host material preparation step may include a step (A-1) of preparing a condensed ring-containing aromatic compound containing a silicon atom mixed therein and a step (A-2) of purifying at least a part of the condensed ring-containing aromatic compound prepared in the step (A-1) to remove at least a part of the silicon atom.

The content of a silicon atom in the condensed ring-containing aromatic compound prepared in the step (A-1) is not particularly limited, and may be, for example, 20 ppm by mass or more, may be 24 ppm by mass or more, may be 50 ppm by mass or more, may be 100 ppm by mass or more, may be 500 ppm by mass or more, may be 1000 ppm by mass or more, may be 5000 ppm by mass or more, may be 10,000 ppm by mass or more. The upper limit of the content of a silicon atom in the condensed ring-containing aromatic compound prepared in the step (A-1) is not particularly limited, and the content may be, for example, 500,000 ppm by mass or less, may be 100,000 mass ppb or less, may be 50,000 ppm by mass or less.

The purification method in the step (A-2) includes the methods exemplified in the above <Method for reducing $C^1$ and $C^H$>.

The content of a silicon atom in the condensed ring-containing aromatic compound after the step (A-2) is usually 2,000 ppm by mass or less, and since the initial deterioration of the light emitting device of the present embodiment is more suppressed, it is preferably 200 ppm by mass or less, more preferably 20 ppm by mass or less, further preferably 10 ppm by mass or less, particularly preferably 5 ppm by mass or less, especially particularly preferably 1 ppm by mass or less, particularly more preferably 0.5 ppm by mass or less, still particularly preferably 0.1 ppm by mass or less, and particularly preferably 0 ppm by mass.

The guest material preparation step may include a preparing step (B-1) of preparing an aromatic amine compound containing a silicon atom mixed therein, and a step (B-2) of purifying at least a part of the aromatic amine compound prepared in the step (B-1) to remove at least a part of the silicon atom.

The content of a silicon atom in the aromatic amine compound prepared in step (B-1) is not particularly limited, and may be, for example, 7.5 ppm by mass or more, may be S ppm by mass or more, may be 20 ppm by mass or more, may be 50 ppm by mass or more, may be 100 ppm by mass or more, may be 500 ppm by mass or more, may be 1000 ppm by mass or more, may be 5000 ppm by mass or more, and may be 10,000 ppm by mass or more. The upper limit of the content of a silicon atom in the aromatic amine compound prepared in the step (B-1) is not particularly limited, and the content may be, for example, 500000 ppm by mass or less, may be 100000 mass ppb or less, and may be 50,000 ppm by mass or less.

The purification method in the step (B-2) includes the methods exemplified in the above <Method for reducing $C^1$ and $C^H$>.

The content of a silicon atom in the aromatic amine compound after the step (B-2) is usually 750 ppm by mass or less, and since the initial deterioration of the light emitting device of the present embodiment is more suppressed, it is preferably 75 ppm by mass or less, more preferably 7.5 ppm by mass or less, further preferably 5 ppm by mass or less, particularly preferably 3 ppm by mass or less, particularly preferably 1 ppm by mass or less, particularly more preferably 0.5 ppm by mass or less, still Particularly preferably 0.1 ppm by mass or less, and particularly preferably 0 ppm by mass.

In the production method (1), in consideration of the amount of a silicon atom contained in the host material and the amount of a silicon atom contained in the guest material, the host material and the guest material are mixed at a compounding ratio at which the sum of them is 20 ppm by mass or less, in the production method. By this, a composition for light emitting device that can suppress the initial deterioration of the light emitting device can be obtained.

In the production step of the production method (1), the method of mixing the host material and the guest material is not particularly limited and includes, for example, a method in which the host material and the guest material are dissolved in the solvent described in the above-described ink section and mixed, a method of mixing the host material and the guest material in a solid state, a method of mixing the host material and the guest material by co-vapor deposition, and the like.

The production method (1) may further include a host material measurement step of measuring the content of a silicon atom contained in the condensed ring-containing aromatic compound. The production method (1) may further include a guest material measurement step of measuring the content of a silicon atom contained in the aromatic amine compound. It is preferable that the production method (1) includes a host material measurement step and a guest material measurement step. In the host material measurement step and the guest material measurement step, the method of measuring the content of a silicon atom is preferably an ICP/MS method.

In the production method (1), the host material measurement step and the guest material measurement step are preferably performed before the production step.

In the production method (1), the host material preparation step preferably includes a host material measurement step. In the production method (1), the guest material preparation step preferably includes a guest material measurement step.

<Production Method (2)>

In another aspect, the method for producing a composition for light emitting device may be a production method of a composition for light emitting device including a host material preparation step of preparing a host material containing a condensed ring-containing aromatic compound, a determination step of determining the compounding ratio of the guest material with respect to the host material, a guest material preparation step of preparing a guest material containing an aromatic amine compound and in which, when mixed with the host material at the above-described compounding ratio, the total amount of a silicon atom contained in the host material and a silicon atom contained in the guest material with respect to the total amount of the host material and the guest material is 20 ppm by mass or less, and a production step of mixing the host material and the guest material at the above-described compounding ratio, to obtain a composition for light emitting device (hereinafter, also referred to as "Production method (2)").

In the production method (2), the host material preparation step may include a step (A-1) of preparing a condensed ring-containing aromatic compound containing a silicon atom mixed therein and a step (A-2) of purifying at least a part of the condensed ring-containing aromatic compound prepared in the step (A-1) to remove at least a part of the silicon atom. The steps (A-1) and (A-2) in the production method (2) may be the same as the steps (A-1) and (A-2) in the above-described production method (1).

In the production method (2), the compounding ratio may be determined according to the characteristics of the light emitting device and the like, in the determination step. In the determination step, for example, the compounding ratio may be determined based on the result of producing a light emitting device using a test composition using materials similar to the host material and the guest material described above, or the compounding ratio may be determined based on the result of producing a light emitting device using a test composition in which the content of a silicon atom is over 20 ppm by mass.

In the production method (2), the content of a silicon atom allowable in the guest material is determined, in the guest material preparation step, depending on the content of a silicon atom in the host material prepared in the host material preparation step and the compounding ratio determined in the determination step. That is, the guest material preparation step can be called a step of preparing a guest material in which the content of a silicon atom is within the allowable range.

In the production method (2), the guest material preparation step may include, for example, a preparation step (B-1) of preparing an aromatic amine compound containing a silicon atom mixed therein, and a step (B-2) of purifying at least a part the aromatic amine compound prepared in the step (B-1) to remove at least a part of the silicon atom. The steps (B-1) and (B-2) in the production method (2) may be the same as the steps (B-1) and (B-2) in the above-described production method (1).

In the production method (2), the host material prepared in the host material preparation step and the guest material prepared in the guest material preparation step are mixed at the compounding ratio determined in the determination step, in the production step. By this, a composition for light emitting device that can suppress the initial deterioration of the light emitting device can be obtained.

The method of mixing the host material and the guest material in the production step of the production method (2) may be the same as the method of mixing the host material and the guest material in the production step of the production method (1).

The production method (2) may further include the above-described host material measurement step. The production method (2) may further include the above-described guest material measurement step. It is preferable that the production method (2) includes the above-described host material measurement step and the above-described guest material measurement step.

In the production method (2), the above-described host material measurement step and the above-described guest material measurement step are preferably performed before the production step.

In the production method (2), the host material preparation step preferably includes the above-described host material measurement step. In the production method (2), the guest material preparation step preferably includes the above-described guest material measurement step.

<Production Method (3)>

In still another aspect, the method for producing a composition for light emitting device may be a production method of a composition for light emitting device including a guest material preparation step of preparing a guest material containing an aromatic amine compound, a determination step of determining the compounding ratio of the host material with respect to the guest material, a host material preparation step of preparing a host material containing a condensed ring-containing aromatic compound and in which, when mixed with the guest material at the above-described compounding ratio, the total amount of a silicon atom contained in the host material and a silicon atom contained in the guest material with respect to the total amount of the host material and the guest material is 20 ppm by mass or less, and a production step of mixing the guest material and the host material at the above-described compounding ratio, to obtain a composition for light emitting device (hereinafter, also referred to as "production method (3)").

In the production method (3), the guest material preparation step may include a step (B-1) of preparing an aromatic amine compound containing a silicon atom mixed therein, and a step (B-2) of purifying at least a part of the aromatic amine compound prepared in the step (B-1) to remove at least a part of the silicon atom. The steps (B-1) and (B-2) in the production method (3) may be the same as the steps (B-1) and (B-2) in the above-described production method (1).

In the production method (3), the compounding ratio may be determined according to the characteristics of the light emitting device, in the determination step. In the determination step, for example, the compounding ratio may be determined based on the result of producing a light emitting device using a test composition using materials similar to the host material and the guest material described above, or the compounding ratio may be determined based on the result of producing a light emitting device using a test composition in which the content of a silicon atom is over 20 ppm by mass.

In the production method (3), the content of a silicon atom allowable in the host material is determined, in the host material preparation step, depending on the content of a silicon atom in the guest material prepared in the guest material preparation step and the compounding ratio determined in the determination step. That is, the host material preparation step can be called a step of preparing a host material in which the content of a silicon atom is within the allowable range.

In the production method (3), the host material preparation step may include, for example, a preparing step (A-1) of preparing a condensed ring-containing aromatic compound containing a silicon atom mixed therein, and a step (A-2) of purifying at least a part of the condensed ring-containing aromatic compound prepared in the step (A-1) to remove at least a part of the silicon atom. The steps (A-1) and (A-2) in the production method (3) may be the same as the steps (A-1) and (A-2) in the above-mentioned production method (1).

In the production method (3), the guest material prepared in the guest material preparation step and the host material prepared in the host material preparation step are mixed at the compounding ratio determined in the determination step, in the production step. By this, a composition for light emitting device that can suppress the initial deterioration of the light emitting device can be obtained.

The method of mixing the host material and the guest material in the production step of the production method (3) may be the same as the method of mixing the host material and the guest material in the production step of the production method (1).

The production method (3) may further include the above-described host material measurement step. The production method (3) may further include the above-described guest material measurement step. It is preferable that the production method (3) includes the above-described host material measurement step and the above-described guest material measurement step.

In the production method (3), the above-described host material measurement step and the above-described guest material measurement step are preferably performed before the production step.

In the production method (3), the host material preparation step preferably includes the above-described host material measurement step. In the production method (3), the guest material preparation step preferably includes the above-described guest material measurement step.

<Production Method (4)>

In still another aspect, the method of producing a composition for light emitting device may be a production method of a composition for light emitting device including a host material preparation step of preparing a condensed ring-containing aromatic compound as the host material, a guest material preparation step of preparing an aromatic amine compound as the guest material, a determination step of determining the compounding ratio of the host material and the guest material, a purification step of purifying at least a part of the condensed ring-containing aromatic compound and the aromatic amine compound so that, when the host material and the guest material are mixed at the above-described compounding ratio, the total amount of a silicon atom contained in the host material and a silicon atom contained in the guest material with respect to the total amount of the host material and the guest material is 20 ppm by mass or less, and a production step of mixing the host material containing the condensed ring-containing aromatic compound and the guest material containing the aromatic amine compound, to obtain a composition for light emitting device (hereinafter, also referred to as "Production method (4)").

In the production method (4), a silicon atom may be mixed in at least one of the condensed ring-containing aromatic compound prepared in the host material preparation step and the aromatic amine compound prepared in the guest material preparation step. That is, the host material preparation step may be a step of preparing a condensed ring-containing aromatic compound in which a silicon atom is mixed, or the guest material preparation step may be a step of preparing an aromatic amine compound in which a silicon atom is mixed.

In the production method (4), the compounding ratio may be determined according to the characteristics of the light emitting device, in the determination step. In the determination step, for example, the compounding ratio may be determined based on the result of producing a light emitting device using a test composition using materials similar to the host material and the guest material described above, the compounding ratio may be determined based on the result of producing a light emitting device using a test composition in which the content of a silicon atom is over 20 ppm by mass, or the compounding ratio may be determined based on the result of producing a light emitting device with a test composition obtained by mixing the condensed ring-containing aromatic compound and the aromatic amine compound prepared in the host material preparation step and the guest material preparation step.

In the production method (4), at least a part of the condensed ring-containing aromatic compound and the aromatic amine compound are purified, in the purification step. The purification method includes the methods exemplified in the above <Method for Reducing $C^1$ and $C^H$>. The purification step may be a step of purifying only one of the condensed ring-containing aromatic compound and the aromatic amine compound, or may be a step of purifying both the condensed ring-containing aromatic compound and the aromatic amine compound.

In the production method (4), the condensed ring-containing aromatic compound and the aromatic amine compound are mixed at the compounding ratio determined in the determination step, in the production step. At this time, since the purification step has been performed, the total amount of a silicon atom contained in the host material and a silicon atom contained in the guest material with respect to the total amount of the host material and the guest material is 20 ppm by mass or less. By this, a composition for light emitting device that can suppress the initial deterioration of the light emitting device can be obtained.

The method of mixing the host material and the guest material in the production step of the production method (4) may be the same as the method of mixing the host material and the guest material in the production step of the production method (1).

The production method (4) may further include the above-described host material measurement step. The production method (4) may further include the above-described guest material measurement step. It is preferable that the production method (4) includes the above-described host material measurement step and the above-described quest material measurement step.

In the production method (4), the above-described host material measurement step and the above-described guest material measurement step are preferably performed before the production step.

In the production method (4), the host material preparation step or the purification step preferably includes the above-described host material measurement step. In the production method (2), the guest material preparation step or the purification step preferably includes the above-described guest material measurement step.

Another aspect of the present invention relates to a method of producing a light emitting device. This production method may be a method of producing a light emitting device containing an anode, a cathode, and an organic layer disposed between the anode and the cathode, including a step of forming the organic layer from the composition for light emitting device produced by any of the above-described production methods (1) to (4)

In the method of producing a light emitting device of the present embodiment, as a method for forming an organic layer, for example, the organic layer can be formed using the same method as for producing a film described above.

Further, in the method of producing a light emitting device of the present embodiment, the production method described in the above-described section <Light emitting device> may be used.

In addition, as the light emitting device in the method of producing a light emitting device of the present embodiment, for example, the light emitting device described in the above-described section <Light emitting device> is mentioned.

EXAMPLES

The present invention will be illustrated further in detail by examples below, but the present invention is not limited to these examples.

In the present examples, the maximum peak wavelength of the emission spectrum of the compound was measured by a spectrophotometer (manufactured by JASCO Corporation, FP-6500) at room temperature. The compound was dissolved in xylene at a concentration of about $0.8 \times 10^{-4}$% by mass to prepare a xylene solution which was then used as a sample. As the excitation light, UV light having a wavelength of 325 nm was used.

In the present examples, the amount of a silicon atom contained in the compound was measured by an ICP emission spectroscopic analysis method.

<Compound H1 and Compound EM1>

A compound H1 was synthesized with reference to a method described in Japanese Unexamined Patent Application Publication (JP-A) No. 2011-105643.

A compound EM1 was synthesized with reference to a method described in International Publication WO 2011/137922.

[Chemical Formula 9]

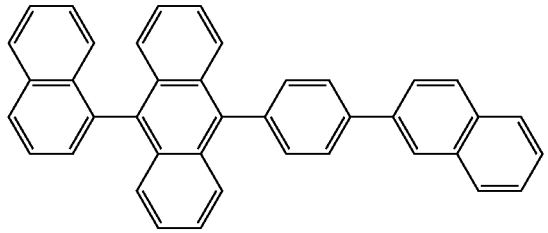

compounds H1 and H2

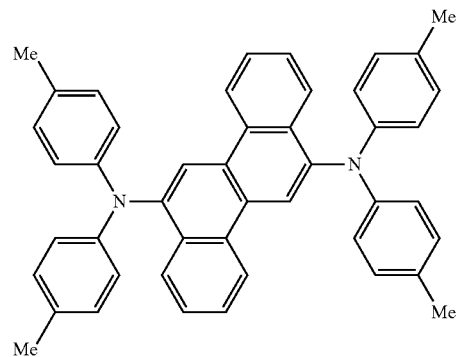

compounds EM1 and EM

The HPLC area percentage value of the compound H1 was 99.5% or more. The amount ($C^H$) of a silicon atom contained in the compound H1 was 24 ppm by mass.

The HPLC area percentage value of the compound EM1 was 99.5% or more. The amount ($C^1$) of a silicon atom contained in the compound EM1 was 8 ppm by mass.

<Purification of Compound H1 (Synthesis of Compound H2)>

A compound H2 was obtained by repeating sublimation purification of the compound H1 until the amount of a silicon atom contained in the compound H1 reached below the detection limit (0 ppm by mass). In sublimation purification, the degree of vacuum was set to $3 \times 10^{-3}$ Pa to $5 \times 10^{-3}$ Pa, and the sublimation temperature was set to 250° C. to 300° C.

The HPLC area percentage value of the compound H2 was 99.5% or more. The amount ($C^H$) of a silicon atom contained in the compound H2 was below the detection limit (0 ppm by mass).

<Purification of Compound EM1 (Synthesis of Compound EM2)>

A compound EM2 was obtained by repeating sublimation purification of the compound EM until the amount of a silicon atom contained in the compound EM1 reached below the detection limit (0 ppm by mass). In sublimation purification, the degree of vacuum was set to $3 \times 10^{-3}$ Pa to $5 \times 10^{-3}$ Pa, and the sublimation temperature was set to 250° C. to 300° C.

The HPLC area percentage value of the compound EM2 was 99.5% or more. The amount ($C^1$) of a silicon atom contained in the compound EM2 was below the detection limit (0 ppm by mass).

The maximum peak wavelength of the emission spectrum of the compounds H1 and H2 was 421 nm. The maximum peak wavelength of the emission spectrum of the compounds EM1 and EM2 was 454 nm.

<Example D1> Fabrication and Evaluation of Light Emitting Device D1

(Formation of Anode and Hole Injection Layer)

An ITO film was attached with a thickness of 45 nm onto a glass substrate by a sputtering method, to form an anode. On the anode, ND-3202 (manufactured by Nissan Chemical Corporation) as a hole injection material was spin-coated, to form a film with a thickness of 35 nm. The substrate carrying the hole injection layer laminated thereon was placed under an air atmosphere, and heated on a hot plate at 50° C. for 3 minutes, and further, heated at 230° C. for 15 minutes, to form a hole injection layer.

(Formation of Hole Transporting Layer)

The polymer compound HTL-1 was dissolved at a concentration of 0.7% by mass in xylene. The resultant xylene solution was spin-coated on the hole injection layer form a film with a thickness of 20 nm, and the film was heated on a hot plate at 180° C. for 60 minutes under a nitrogen gas atmosphere, to form a hole transporting layer. The polymer compound HTL-1 is a polymer compound in Polymer Example 1 of International Publication WO2014/102543.

(Formation of Light Emitting Layer)

The compound H2 and the compound EM2 (compound H2/compound EM2=90% by mass/10% by mass) were dissolved at a concentration of 2% by mass in toluene. The resultant toluene solution was spin-coated on the hole transporting layer to form a film with a thickness of 60 nm, and the film was heated at 130° C. for 10 minutes under a nitrogen gas atmosphere, to form a light emitting layer.

(Formation of Cathode)

The substrate carrying the light emitting layer formed thereon was placed in a vapor deposition machine, and the pressure in the machine was reduced to $1.0 \times 10^{-4}$ Pa or less, then, as cathode, sodium fluoride was vapor-deposited with a thickness of about 4 nm on the light emitting layer, then, aluminum was vapor-deposited with a thickness of about 80 nm on the sodium fluoride layer. After vapor deposition, sealing with a glass substrate was performed, to fabricated a light emitting device D1.

(Evaluation of Light Emitting Device)

Voltage was applied to the light emitting device D1, to observe EL emission. The device was driven at constant current at 150 mA/cm², and the time until the luminance reached 95% (hereinafter, referred to also as "LT95") was measured.

Examples D2 to D6 and Comparative Example CD1

Fabrication and Evaluation of Light Emitting Devices D2 to D6 and CD1

Light emitting devices D2 to D6 and CD1 were fabricated in the same manner as in Example D1, except that materials described in Table 1 were used at the material ratios described in Table 1 instead of "compound H2 and compound EM2 (compound H2/compound EM2=90% by mass/10% by mass)" in (Formation of light emitting layer) of Example D1.

Voltage was applied to the light emitting devices D2 to D6 and CD1, to observe EL emission. LT95 of the light emitting devices D2 to D6 and CD1 was measured.

The results of Examples D1 to D6 and Comparative Example CD1 are shown in Table 1. The relative values of LT95 of the light emitting devices D1 to D6 when LT95 of the light emitting device CD1 is set to 1.0 are shown.

TABLE 1

| | light emitting device | material | light emitting layer material ratio (% by mass) | $C^H$ (ppm by mass) | $C^1$ (ppm by mass) | $C^H W^H + C^1 W^1$ (ppm by mass) | LT95 (relative value) |
|---|---|---|---|---|---|---|---|
| Example D1 | D1 | H2/EM2 | 90/10 | 0 | 0 | 0 | 2.7 |
| Example D2 | D2 | H2/EM2/EM1 | 90/7/3 | 0 | 2.4 | 0.24 | 2.0 |
| Example D3 | D3 | H2/H1/EM2 | 88/2/10 | 0.53 | 0 | 0.48 | 2.0 |
| Example D4 | D4 | H2/EM2/EM1 | 90/1/9 | 0 | 7.2 | 0.72 | 1.6 |
| Example D5 | D5 | H2/H1/EM2 | 72/18/10 | 4.8 | 0 | 4.3 | 1.7 |
| Example D6 | D6 | H2/H1/EM2 | 18/72/10 | 19.2 | 0 | 17.3 | 1.3 |
| Comparative Example CD1 | CD1 | H1/EM1 | 90/10 | 24 | 8 | 22.4 | 1.0 |

INDUSTRIAL APPLICABILITY

According to this invention, a composition which is useful for production of a light emitting device in which the initial deterioration is suppressed is provided. The present invention is industrially useful because the production of a light emitting device in which initial deterioration is suppressed has effects such as resource saving, energy saving and the like.

The invention claimed is:

1. A method of producing a composition for a light emitting device containing a host material and a guest material blended, comprising
a host material preparation step of preparing a host material containing an aromatic compound having a condensed ring skeleton in which only three or more benzene rings are condensed,
a guest material preparation step of preparing a guest material containing an aromatic amine compound represented by formula (FB), and
a production step of mixing said host material and said guest material at a compounding ratio by which the total amount of a silicon atom contained in said host material and a silicon atom contained in said guest material is 20 ppm by mass or less, to obtain a composition for a light emitting device;
wherein said guest material preparation step comprises
a preparation step (B-1) of preparing said aromatic amine compound containing a silicon atom mixed therein, and a step (B-2) of subliming at least a part of said aromatic amine compound prepared in said step (B-1) to remove at least a part of said silicon atom; and wherein said host material preparation step comprises a step (A-1) of preparing said aromatic compound containing a silicon atom mixed therein, and a step (A-2) of subliming at least a part of said aromatic compound prepared in said step (A-1) to remove at least a part of said silicon compound;

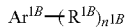
$$Ar^{1B}-(R^{1B})_{n1B} \quad (FB)$$

wherein $n^{1B}$ represents an integer of 2 or more, $Ar^{1B}$ represents an aromatic hydrocarbon group or an aromatic heterocyclic group, and the foregoing groups optionally have a substituent, and when a plurality of the substituents are present, they may be the same or different and may be combined together to form a ring together with atoms to which they are attached, $R^{1B}$ represents an amino group or a substituted amino group, and the foregoing groups optionally have a substituent, and when a plurality of the substituents are present, they may be the same or different and may be combined together to form a ring together with atoms to which they are attached, and when a plurality of $R^{1B}$ are present, they may be the same or different and may be combined together to form a ring together with atoms to which they are attached.

2. A method of producing a composition for a light emitting device containing a host material and a guest material blended, comprising a host material preparation step of preparing a host material containing an aromatic compound having a condensed ring skeleton in which only three or more benzene rings are condensed, a guest material preparation step of preparing a guest material containing an aromatic amine compound, a determination step of determining the compounding ratio of said host material and said guest material, a purification step of subliming at least a part of said aromatic compound and at least a part of said aromatic amine compound so that, when said host material and said guest material are mixed at said compounding ratio, the total amount of a silicon atom contained in said host material and a silicon atom contained in said guest material with respect to the total amount of said host material and said guest material is 20 ppm by mass or less, and a production step of mixing said host material containing said aromatic compound and said guest material containing said aromatic amine compound, to obtain a composition for a light emitting device;

wherein said guest material preparation step comprises a preparation step (B-1) of preparing said aromatic amine compound containing a silicon atom mixed therein, and a step (B-2) of subliming at least a part of said aromatic amine compound prepared in said step (B-1) to remove at least a part of said silicon atom; and wherein said host material preparation step comprises a step (A-1) of preparing said aromatic compound containing a silicon atom mixed therein, and a step (A-2) of subliming at least a part of said aromatic compound prepared in said step (A-1) to remove at least a part of said silicon compound.

3. The production method according to claim 1, further comprising a host material measurement step of measuring the content of a silicon atom contained in said aromatic compound, and a guest material measurement step of measuring the content of a silicon atom contained in said aromatic amine compound.

4. A method of producing a light emitting device containing an anode, a cathode and an organic layer disposed between said anode and said cathode, comprising a step of forming said organic layer from a composition for light emitting device produced by the production method according to claim 1.

* * * * *